(12) United States Patent
Naveh et al.

(10) Patent No.: US 11,751,813 B2
(45) Date of Patent: Sep. 12, 2023

(54) SYSTEM, METHOD AND COMPUTER PROGRAM PRODUCT FOR DETECTING A MOBILE PHONE USER'S RISKY MEDICAL CONDITION

(71) Applicant: Celloscope Ltd., Tel Aviv (IL)

(72) Inventors: Yuval Naveh, Haifa (IL); Shahar Davidson, Rehovot (IL); Tomer Shussman, Kfar Saba (IL)

(73) Assignee: CELLOSCOPE LTD., Tel Aviv (IL)

( * ) Notice: Subject to any disclaimer, the term of this patent is extended or adjusted under 35 U.S.C. 154(b) by 407 days.

(21) Appl. No.: 16/814,114

(22) Filed: Mar. 10, 2020

(65) Prior Publication Data

US 2020/0375544 A1  Dec. 3, 2020

Related U.S. Application Data

(63) Continuation-in-part of application No. 16/659,832, filed on Oct. 22, 2019.
(Continued)

(51) Int. Cl.
*G06F 15/16* (2006.01)
*G06Q 50/00* (2012.01)
(Continued)

(52) U.S. Cl.
CPC .......... *A61B 5/6898* (2013.01); *A61B 5/0077* (2013.01); *A61B 5/112* (2013.01);
(Continued)

(58) Field of Classification Search
CPC ..... A61B 5/6898; A61B 5/0077; A61B 5/112; A61B 5/4064; A61B 5/4803; A61B 5/681;
(Continued)

(56) References Cited

U.S. PATENT DOCUMENTS

| 7,558,622 B2 | 7/2009 | Tran |
| 7,647,196 B2 | 1/2010 | Kahn et al. |

(Continued)

FOREIGN PATENT DOCUMENTS

| EP | 3107452 A | 12/2016 |
| EP | 3107452 A1 | 12/2016 |

OTHER PUBLICATIONS www.csmonitor.com/World/Passcode/2016/1222/How-smartphones-could-prevent-drunk-driving—Dec. 22, 2016.
(Continued)

*Primary Examiner* — Tanmay K Shah
(74) *Attorney, Agent, or Firm* — Browdy and Neimark, PLLC

(57) ABSTRACT

A stroke detection system operative to detect strokes suffered by mobile communication device users, the system including a hardware processor operative in conjunction with a mobile communication device having at least one built-in sensor. The hardware processor is configured to, repeatedly and without being activated by the device's user, compare data derived from the at least one sensor to at least one baseline value for at least one indicator of user well-being, stored in memory accessible to the processor and/or make a stroke risk level evaluation; and/or perform at least one action if and only if the stroke risk level is over a threshold.

26 Claims, 15 Drawing Sheets

Related U.S. Application Data

(60) Provisional application No. 62/816,227, filed on Mar. 11, 2019.

(51) Int. Cl.
 *A61B 5/00* (2006.01)
 *A61B 5/11* (2006.01)
 *A61B 5/024* (2006.01)

(52) U.S. Cl.
 CPC .......... *A61B 5/4064* (2013.01); *A61B 5/4803* (2013.01); *A61B 5/681* (2013.01); *A61B 5/7275* (2013.01); *A61B 5/7435* (2013.01); *A61B 5/02438* (2013.01); *A61B 2560/0462* (2013.01); *A61B 2562/0204* (2013.01); *A61B 2562/0219* (2013.01); *A61B 2562/06* (2013.01)

(58) Field of Classification Search
 CPC . A61B 5/7275; A61B 5/7435; A61B 5/02438; A61B 2560/0462; A61B 2562/0204; A61B 2562/0219; A61B 2562/06
 USPC .......................................................... 709/203
 See application file for complete search history.

(56) References Cited

U.S. PATENT DOCUMENTS

| | | | |
|---|---|---|---|
| 9,443,063 | B2 | 9/2016 | Ghassemzadeh et al. |
| 9,700,241 | B2 | 7/2017 | Eastman et al. |
| 9,727,698 | B2 | 8/2017 | Ghassemzadeh et al. |
| 9,872,637 | B2 | 1/2018 | Kording et al. |
| 9,974,478 | B1 * | 5/2018 | Brokaw ................. A61B 5/486 |
| 10,231,651 | B2 | 3/2019 | Deng et al. |
| 10,307,086 | B2 | 6/2019 | Cheung |
| 10,342,462 | B2 | 7/2019 | Martin |
| 10,548,512 | B2 | 2/2020 | Hausdorff et al. |
| 10,629,048 | B2 | 4/2020 | Tan et al. |
| 10,750,977 | B2 | 8/2020 | Kording et al. |
| 10,765,347 | B2 | 9/2020 | Fuke et al. |
| 11,058,327 | B2 | 7/2021 | Shuster et al. |
| 11,096,577 | B2 * | 8/2021 | Davis, III ............ A61B 5/0002 |
| 11,213,224 | B2 | 1/2022 | Dohrmann et al. |
| 2014/0156215 | A1 | 6/2014 | Eastman et al. |
| 2015/0196231 | A1 | 7/2015 | Ziaie et al. |
| 2015/0230734 | A1 | 8/2015 | Cheung |
| 2015/0366518 | A1 * | 12/2015 | Sampson ............. A61B 5/0205 600/509 |
| 2017/0007167 | A1 * | 1/2017 | Kostic .................. A61B 5/4064 |
| 2017/0105014 | A1 | 4/2017 | Lee et al. |
| 2017/0105104 | A1 * | 4/2017 | Ulmansky ............... H04W 4/42 |
| 2017/0270252 | A1 * | 9/2017 | Feit ......................... H04W 4/90 |
| 2017/0270262 | A1 | 9/2017 | Noh et al. |
| 2018/0220935 | A1 | 8/2018 | Tadano et al. |
| 2018/0253530 | A1 * | 9/2018 | Goldberg ............. A61B 5/4803 |
| 2018/0296092 | A1 | 10/2018 | Hassan et al. |
| 2020/0046263 | A1 | 2/2020 | Hauenstein et al. |
| 2020/0170548 | A1 | 6/2020 | Hausdorff et al. |
| 2020/0289027 | A1 | 9/2020 | Naveh et al. |
| 2020/0375544 | A1 | 12/2020 | Naveh et al. |
| 2021/0393162 | A1 | 12/2021 | Crocker et al. |
| 2021/0393166 | A1 | 12/2021 | DeMers et al. |
| 2022/0262224 | A1 | 8/2022 | Hanson et al. |
| 2022/0262492 | A1 | 8/2022 | Vaccaro |

OTHER PUBLICATIONS www.buffalo.edu/news/releases/2018/10/010.html—Oct. 3, 2018.
Garcia, L., Tomás, J., Parra, L., & Lloret, J. (2019). An m-health application for cerebral stroke detection and monitoring using cloud services. International Journal of Information Management, 45, 319-327.
en.wikipedia.org/w/index.php?title=Wearable_technology&oldid=886292852#Usage—Mar. 5, 2019.
en.wikipedia.org/w/index.php?title=Azumio&oldid-885386796—Feb. 27, 2019.
www.nyu.edu/classes/dat-fall2014/potential-projects/art-biofeedback/—2014.
completespeech.com/speechracer/—2018.
www.wsj.com/articles/new-speech-therapy-tools-make-practicing-at-home-easier-1402061561—Jun. 8, 2014.
www.mobihealthnews.com/20155/dods-new-android-app-connects-to-wearable-devices-for-biofeedback—Feb. 34,2013.
www.ncbi.nlm.nih.gov/pubmed/24507934—Jan. 18, 2014.
www.ncbi.nlm.nih.gov/pubmed/24041610—Sep. 14, 2013.
Perry, J., & Davids, J. R. (1992). Gait analysis: normal and pathological function. Journal of Pediatric Orthopaedics, 12 (6), 815.
gaitup.com/—2013.
www.xsens.com/—2017.
Giansanti, D., Maccioni, G., & Macellari, V. (2005). The development and test of a device for the reconstruction of 3-D position and orientation by means of a kinematic sensor assembly with rate gyroscopes and accelerometers. IEEE transactions on biomedical engineering, 52(7), 1271-1277.
Gastaldi, L., Rosso, V., Gabola, V., Agostini, V., Frutos, M. L., Knaflitz, M., . . . & Tadano, S. (May 2016). Technical challenges using magneto-inertial sensors for gait analysis. In 2016 IEEE International Symposium on Medical Measurements and Applications (MeMeA) (pp. 1-6). IEEE.
Teufl, W., Lorenz, M., Miezal, M., Taetz, B., Fröhlich, M., & Bleser, G. (2019). Towards inertial sensor based mobile gait analysis: Event-detection and spatio-temporal parameters Sensors, 19(1), 38.
Ellis, R. J., Ng, Y. S., Zhu, S., Tan, D. M., Anderson, B., Schlaug, G., & Wang, Y. (2015). A validated smartphone-based assessment of gait and gait variability in Parkinson's disease. PLoS one, 10(10), e0141694.
Cereatti, A., Trojaniello, D., & Della Croce, U. (Mar. 2015). Accurately measuring human movement using magneto-inertial sensors: techniques and challenges. In 2015 IEEE International Symposium on Inertial Sensors and Systems (ISISS) Proceedings (pp. 1-4). IEEE.
Wang, Jindong, et al. "Deep learning for sensor-based activity recognition: A survey." Pattern Recognition Letters 119 (2019): 3-11.
Ordóñez, Francisco, and Daniel Roggen. "Deep convolutional and LSTM recurrent neural networks for multimodal wearable activity recognition " Sensors 16.1 (2016): 115.
Murad, Abdulmajid, and Jae-Young Pyun. "Deep recurrent neural networks for human activity recognition." Sensors 17.11 (2017): 2556.
Gadaleta, Matteo, and Michele Rossi. "Idnet: Smartphone-based gait recognition with convolutional neural networks." Pattern Recognition 74 (2018): 25-37.
Silsupadol, Patima, Kunlanan Teja, and Vipul Lugade. "Reliability and validity of a smartphone-based assessment of gait parameters across walking speed and smartphone locations: Body, bag, belt, hand, and pocket." Gait & posture 58 (2017): 516-522).
How, T. V., Chee, J., Wan, E., & Mihailidis, A. (May 2013). MyWalk: a mobile app for gait asymmetry rehabilitation in the community. In 2013 7th International Conference on Pervasive Computing Technologies for Healthcare and Workshops (pp. 73-76). IEEE.
Perez, Andres A., and Miguel A. Labrador. "A smartphone-based system for clinical gait assessment." 2016 IEEE International Conference on Smart Computing (Smartcomp). IEEE, 2016.
Fuld, Hillel's Tech Corner: Tel Aviv start-up taking tech one step further, Jerusalem Post, pp. 1-4 (2020).
Ogawara et al., Detecting Repeated Motion Patterns via Dynamic Programming using Motion Density, 2009 IEEE International Conference on Robotics and Automation, Kobe International Conference Center, pp. 1743-1749, Kobe, Japan, May 12-17, 2009.
Brownlee, A Gentle Introduction to Padding and Stride for Convolutional Neural Networks, downloaded from https://machinelearningmastery.com/padding-and-stride-for-convolutionalneural-networks/, Aug. 16, 2019.

(56) References Cited

OTHER PUBLICATIONS

Quaternions and spatial rotation, downloaded from en.wikipedia.org/wiki/Quaternions_and_spatial_rotation (Nov. 8, 2022).

Murphy et al., Three-dimensional kinematic motion analysis of a daily activity drinking from a glass: a pilot study, Journal of NeuroEngineering and Rehabilitation, Article No. 18, downloaded from https://jneuroengrehab.biomedcentral.com/articles/10.1186/1743-0003-3-18 (2006).

Mehta et al., XNect: Real-time Multi-Person 3D Motion Capture with a Single RGB Camera, ACM Trans. Graph., 39 (4)Article 1:1-1:24 (2020).

Chun et al., BVH Motion Capture Data Animated downloaded from www.cs.cityu.edu.hk/~howard/Teaching/CS4185-5185-2007-SemA/Group12/BVH.html (2007).

Mahfuz et al., Detecting Irregular Patterns in IoT Streaming Data for Fall Detection, downloaded from www.researchgate.net/publication/329033123_Detecting_Irregular_Patterns_in_IoT_Streaming_Data_for_Fall_Detection (2018).

Padding and Stride, downloaded from d2I.ai/chapter_convolutional-neural-networks/padding-andstrides.html (2019).

Motion capture, Wikipedia, pp. 1-15, downloaded from en.wikipedia.org/wiki/Motion_capture (Nov. 27, 2022).

BVH File Extension, pp. 1-9, downloaded from www.file-extension.info/format/bvh, (2014-2022).

Motion Capture with you smartphone, Rush Motion, pp. 1-8, downloaded from rush-motion.com/ (2022).

Zetter, K. How smartphones could prevent drunk driving, The Christian Science Monitor, downloaded from https://www.csmonitor.com/World/Passcode/2016/1222/Howsmartphones-could-prevent-drunk-driving Dec. 22, 2016.

Nealon, Portable cancer test uses smartphone, new gold biosensor, University at Buffalo, download from—https://www.buffalo.edu/news/releases/2018/10/010.html (2018).

Garcia et al., An m-health application for cerebral stroke detection and monitoring using cloud services. International Journal of Information Management, 45:319-327 (2019).

Azumio, Wikipedia, downloaded from https://en.wikipedia.org/wiki/Azumio (Jul. 17, 2022).

Catherine Rehwinkel, 4D VR Grid (Multi-axis 360 degree perspectives and space/time transitions, downloaded from https://itp.nyu.edu/classes/dat-fall2014/potential-projects/art-biofeedback/, 38 pages (2016).

SpeechRacer2, downloaded from completespeech.com, 4 pages (2022).

Johnson, New Speech-Therapy Tools Make Practicing at Home Easier—downloaded from https://www.wsj.com/articles/new-speech-therapy-tools-make-practicing-athome-easier-1402061561, 5 pages (2014).

Comstock, DoD's new Android app connects to wearable devices for biofeedback, downloaded from https://www.mobihealthnews.com/20155/dods-new-android-app-connectsto-wearable-devices-for-biofeedback, 12 pages (2013).

Berssenbrügge, et al., 2D and 3D analysis methods of facial asymmetry in comparison. Journal of Cranio-Maxillofacial Surgery, 42(6), e327-e334 (2014).

Berlin et al. Quantification of facial asymmetry by 2D analysis—A comparison of recent approaches. Journal of Cranio-Maxillofacial Surgery, 42.3:265-271 (2014).

Giansanti et al., The development and test of a device for the reconstruction of 3-D position and orientation by means of a kinematic sensor assembly with rate gyroscopes and accelerometers. IEEE transactions on biomedical engineering, 52(7):1271-1277 (2005).

Rosso et al., Technical challenges using magneto-inertial sensors for gait analysis. In 2016 IEEE International Symposium on Medical Measurements and Applications (MeMeA) (pp. 1-2). IEEE (May 2016).

Teufl et al., Towards inertial sensor based mobile gait analysis:event-detection and spatio-temporal parameters, Sensors, 19(1):38 (2019).

Ellis et al., A validated smartphone-based assessment of gait and gait variability in Parkinson's disease, PLoS one 10.10:e0141694 (2015).

Cereatti et al., Accurately measuring human movement using magneto-inertial sensors: techniques and challenges, IEEE International Symposium on Inertial Sensors and Systems (ISISS) Proceedings IEEE, 2015.

Wang et al. Deep learning for sensor-based activity recognition: A survey, Pattern Recognition Letters 119:3-11 (2019).

Ordóñez et al., Deep convolutional and LSTM recurrent neural networks for multimodal wearable activity recognition, Sensors, 16(1):115(2016).

Murad, et al., Deep recurrent neural networks for human activity recognition, Sensors 17(11):2556 (2017).

Gadaleta et al., Idnet: Smartphone-based gait recognition with convolutional neural networks. Pattern Recognition 74:25-37 (2018).

Silsupadol, et al., Reliability and validity of a smartphone-based assessment of gait parameters across walking speed and smartphone locations: Body, bag, belt, hand, and pocket, Gait & posture 58: 56-522 (2017).

Digital motion analytics platform—Digital motion analytics platform, Physiology, downloaded from https://gaitup.com/ (2023).

How et al., MyWalk: a mobile app for gait asymmetry rehabilitation in the community. In 2013 7th International Conference on Pervasive Computing Technologies for Healthcare and Workshops (pp. 73-76) IEEE (2013).

Perry, et al., Gait analysis: normal and pathological function. Journal of Pediatric Orthopaedics, 12(6):815 (1992).

Perez et al., A smartphone-based system for clinical gait assessment, 2016 IEEE International Conference on Smart Computing (Smartcomp). IEEE, 2016.

Wearable technology, Wikipedia, downloaded from https://en.wikipedia.org/w/index.php?oldid=886292852&title=Wearable_technology#Usage (2019).

Motion Capture, downloaded from https://www.xsens.com/, 6 pages (2017).

* cited by examiner

Fig. 9

900 – onetime registration process

↓

901 – flow of data (and passive signals) including all or any subset of operations a, b, c in Fig. 10

↓

902 – validation test outputs (user cooperation = active signals) which may include operation e of Fig. 10

↓

903 – health condition monitoring: gets passive and active signals, updates norms, estimates health condition and risk. May include operation d of Fig. 10.

↓

904 –activation of action component e.g. as described herein with reference to operations e, h of Fig. 10 and/or change of sensors' triggering e.g. as described herein with reference to operations f, g of Fig. 10.

Fig. 10

A0. system collects offline information re mobile phone user

a. monitoring: Data from sensors, if active, flow into system

b1. data from operation a is used to identify user's activity type/s

b2. data from operation a compared to activities detected in b1 used to Identify device's bodily position

c1. Deduce (e.g. extract from tables stored in memory) which signals are available given b1 and b2.

c2. extraction of signals deemed available in operation c1, from sensors' data from operation a

d. Signals from c2 and, if available, at least one output from operation e may be used by system to estimate risk of emergency

e. if the risk estimated in operation d triggers a threshold condition, take action
System may go back to d

f. System collects contextual info such as location, and access of medical services to the user

g. If risk estimated in operation d or e fulfils a threshold condition, system contacts family member, caregiver or medical services taking into account contextual situation collected in operation f.

h. Risk estimated in operation d or e used by system to determine schedule by which (or frequency at which) to trigger sensor activation.

Fig. 11

Operation 1110: Definition of signal generation functions used to extract signals from the raw data e.g.
    a. When a signal is available; and/or
    b. Training the generation of signals e.g. using a Machine learning algorithm

↓

Operation 1120: Settings of condition estimation automat/component/ functionality e.g.
    c. Definition of states and/or
    d. Fitting the automat dynamics: transition between states and probability functions of signals' values

↓

Operation 1130: Implementation of actions e.g. all or any subset of
    e. User cooperation tests
    f. User notifications
    g. Service to contact with
    h. Contextual information to collect
    i. Timing mechanism of the sensors

SYSTEM, METHOD AND COMPUTER PROGRAM PRODUCT FOR DETECTING A MOBILE PHONE USER'S RISKY MEDICAL CONDITION

REFERENCE TO CO-PENDING APPLICATIONS

Priority is claimed from the following US applications, the disclosures of which applications is hereby incorporated by reference: "System For Detecting A Risky Medical Condition Of A User", U.S. Ser. No. 62/816,227 filed 11 Mar. 2019; and "System, Method And Computer Program Product For Assessment Of A User's Gait", U.S. Ser. No. 16/659,832, filed 22 Oct. 2019.

FIELD OF THIS DISCLOSURE

The present invention relates generally to cellphones, and more particularly to processing outputs of cellphone sensors.

BACKGROUND FOR THIS DISCLOSURE

Conventional technology constituting background to certain embodiments of the present invention is described in the following publications inter alia:

The following reference https://www.csmonitor.com/World/Passcode/2016/1222/How-smartphones-could-prevent-drunk-driving describes smartphone-based detection of intoxication vs a state of sobriety: "Alcohol distinctly affects movement, gait, and balance in ways that can be detected by the built-in motion sensors on devices people carry around with them all the time". The reference notes that "The technology could also be designed to communicate with connected cars to prevent vehicles from starting if the data from sensors determines the device-wearer is drunk" and suggests a situation in which "an employer or insurance company requires access to the data as a condition of employment or an insurance policy". The reference describes devices which "have five built-in motion sensors an accelerometer, a gyroscope, linear acceleration, gravity, and compass."

Systems that detect medical problems using smartphones are known, e.g. smartphone-based systems which detect cancer (http://www.buffalo.edu/news/releases/2018/10/010.html); and
https://patents.google.com/patent/EP3107452A1/en?oq=asymmetric+gait+smartphone
https://patents.google.com/patent/US20140156215?oq=asymmetric+gait+smartphone
Healthymize describes COPD monitoring, e.g. here;
https://patents.google.com/patent/US20180296092A1/en?assignee=healthymize&oq=healthymize
Active stroke detection is described e.g. here:
https://www.sciencedirect.com/science/article/pii/S0268401218302780
Wiki says that:
"Wearables can be used to collect data on a user's health including:
Heart rate
Calories burned
Steps walked
Blood pressure
Time spent exercising".

Azumio is an enterprise which attempts to "turn phones into biofeedback devices" without using any external hardware (see e.g. https://en.wikipedia.org/wiki/Azumio). However, Azumio requires the user to proactively activate its functionalities rather than operating passively. For example, if the user places her or his finger on the camera lens, the Azumio app may capture biometric indications of stress. Or, if the user places the phone on his bed and activates another accelerometer reliant Azumio app, this app may measure, say, how much the end-user is moving during the night.

Speech Therapy apps providing feedback to users include:
https://itp.nyu.edu/classes/dat-fall2014/potential-projects/art-biofeedback/
https://completespeech.com/speechracer/
https://www.wsj.com/articles/new-speech-therapy-tools-make-practicing-at-home-easier-1402061561
The following reference: https://www.mobihealthnews.com/20155/dods-new-android-app-connects-to-wearable-devices-for-biofeedback describes mobile biofeedback, which uses a smartphone in conjunction with additional external hardware, typically wireless commercially available sensors with open APIs such as electroencephalogram (EEG), electrocardiogram (ECG), electromyography, galvanic skin response, respiratory rate, and skin temperature.

Quantification of facial asymmetry based on a 2d image of the face can use any suitable known technique, such as those described in https://www.ncbi.nlm.nih.gov/pubmed/24507934 or https://www.ncbi.nlm.nih.gov/pubmed/24041610.

The disclosures of all publications and patent documents mentioned in the specification, and of the publications and patent documents cited therein directly or indirectly, are hereby incorporated by reference other than subject matter disclaimers or disavowals. If the incorporated material is inconsistent with the express disclosure herein, the interpretation is that the express disclosure herein describes certain embodiments, whereas the incorporated material describes other embodiments. Definition's within the incorporated material may be regarded as one possible definition for the term/s in question.

SUMMARY OF CERTAIN EMBODIMENTS

Certain embodiments of the present invention seek to provide circuitry typically comprising at least one processor in communication with at least one memory, with instructions stored in such memory executed by the processor to provide functionalities which are described herein in detail. Any functionality described herein may be firmware-implemented or processor-implemented, as appropriate.

Certain embodiments of the present invention seek to provide a system, method and computer program product for detecting a mobile phone user's medical condition e.g. to detect that a user may be having a stroke.

Certain embodiments of the present invention seek to provide a system which, at least once, initiates user cooperation to validate (or modify) the system's current estimation of a user's condition.

Certain embodiments of the present invention seek to provide a system which, at least once, activates an inactive sensor in a user's mobile phone, responsive to a current estimation of a user's condition derived from data provided by sensors other than the inactive sensor in the user's mobile phone, and validates or modifies the current estimation of a user's condition, according to outputs of the inactive sensor. This is advantageous inter alia because the system may initiate or activate different sources of information to validate its estimations. This enhances the system's efficiency and accuracy—compared to a system capable only of activating a single source of data and analyzing only that source, all the time.

Certain embodiments of the present invention seek to provide a system which is configured to trigger or activate or change sampling frequency of certain sensor/s responsive to outputs from other sensor/s. For example, an accelerometer, which may always be on, may detect some kind of motion such as walking, going up stairs or any other repetitive motion, and the system, or an action component thereof, may responsively activate the gyroscope to arrive at a more precise conclusion such as angular motion patterns including, for example, range of flexion and extension of the thigh movement, and/or the system, or an action component thereof, may, e.g. responsive to the outputs from the accelerometer and/or gyroscope, activate the camera to get a still or video of the user's face (for extracting more information) when the user next interacts with his phone, perhaps first activating a sound production device in the phone to fire a loud notification for getting the user's attention, thereby to encourage interaction of the user with his phone, if the user is capable of cooperating.

Certain embodiments of the present invention seek to provide a biofeedback system operative to provide real-time feedbacks to improve a mobile communication device user's behavior, the system comprising a hardware processor operative in conjunction with a mobile communication device having at least one built-in sensor; the hardware processor being configured to, repeatedly and without being activated by the device's user, respond to data derived from the at least one sensor, the data characterizing a behavior of the mobile communication device user, by providing real-time feedbacks to the user regarding her or his behavior, thereby to facilitate self-improvement of the behavior by the user. The behavior may include speech or walking, e.g. in the course of a speech therapy or walking rehabilitation process, respectively.

It is appreciated that any reference herein to, or recitation of, an operation being performed is, e.g. if the operation is performed at least partly in software, intended to include both an embodiment where the operation is performed in its entirety by a server A, and also to include any type of "outsourcing" or "cloud" embodiments in which the operation, or portions thereof, is or are performed by a remote processor P (or several such), which may be deployed off-shore or "on a cloud", and an output of the operation is then communicated to, e.g. over a suitable computer network, and used by, server A. Analogously, the remote processor P may not, itself, perform all of the operations, and, instead, the remote processor P itself may receive output/s of portion/s of the operation from yet another processor's may be deployed off-shore relative to P, or "on a cloud", and so forth.

The Present Invention Typically includes at Least the Following Embodiments:

Embodiment 1. A stroke detection system operative to detect strokes suffered by mobile communication device users, the system comprising: a hardware processor operative in conjunction with a mobile communication device having at least one built-in sensor; the hardware processor being configured to, typically repeatedly and typically without being activated by the device's user, compare data derived from the at least one sensor to at least one baseline value for at least one indicator of user well-being, stored in memory accessible to the processor, and/or make a stroke risk level evaluation; and/or perform at least one action if and only if the stroke risk level is over a threshold.

Embodiment 2. The system of any of the preceding embodiments wherein the system initiates user cooperation to validate the evaluation and changes the evaluation for at least one user, responsive to that user's cooperation.

Embodiment 3. The system of any of the preceding embodiments wherein the system connects to at least one additional wearable to validate the evaluation, and changes the evaluation for at least one user, responsive to data provided by the at least one additional wearable.

Embodiment 4. The system of any of the preceding embodiments wherein the wearable comprises a smartwatch, pedometer, or heartbeat monitor.

Embodiment 5. The system of any of the preceding embodiments wherein the at least one sensor comprises plural sensors.

Embodiment 6. The system of any of the preceding embodiments wherein the plural sensors include at least one of the following: IMU, camera, microphone.

Embodiment 7. The system of any of the preceding embodiments wherein the plural sensors include at least two of the following: MU, camera, microphone.

Embodiment 8. The system of any of the preceding embodiments wherein the system is configured, at least once, to activate an inactive sensor in a user's mobile phone, responsive to a current estimation of a user's condition derived from data provided by sensors other than the inactive sensor in the user's mobile phone, and validates or modifies the current estimation of a user's condition, according to outputs of the inactive sensor.

Embodiment 9. The system of any of the preceding embodiments wherein the system is configured to document at least one temporary infrequent symptom such as TIA.

Embodiment 10. The system of any of the preceding embodiments wherein the sensor comprises a motion sensor.

Embodiment 11. The system of any of the preceding embodiments wherein the motion sensor comprises at least one of: gyroscope, accelerometer.

Embodiment 12. The system of any of the preceding embodiments wherein the sensor comprises at least one of: camera, microphone, or keypad of the communication device.

Embodiment 13. The system of any of the preceding embodiments wherein the stroke risk level evaluation includes detection of facial asymmetry which differs from the indicator.

Embodiment 14. The system of any of the preceding embodiments wherein the stroke risk level evaluation relies only on the at least one built-in sensor, thereby to obviate any need for any sensor not already deployed in mobile phones.

Embodiment 15. The system of any of the preceding embodiments wherein the action comprises prompting the user to cooperate in a validation process.

Embodiment 16. The system of any of the preceding embodiments wherein an auxiliary software platform enables recruitment of mobile phone users to subscribe to the system, thereby to allow an organization affiliated with a multiplicity of mobile phone users, to require or incentivize mobile phone users affiliated therewith to subscribe to the system.

Embodiment 17. The system of any of the preceding embodiments wherein the data comprises gait analysis data.

Embodiment 18. The system of any of the preceding embodiments wherein the stroke risk level evaluation includes processing the gait analysis data including detection of gait asymmetry which differs from the indicator.

Embodiment 19. The system of any of the preceding embodiments wherein the hardware processor comprises the mobile communication device's processor, onto which cell. app software has been downloaded, wherein the software is configured to:

compare data derived from the at least one sensor to at least one baseline value for at least one indicator of user well-being, stored in memory accessible to the processor, make a stroke risk level evaluation; and perform at least one action if and only if the stroke risk level is over a threshold.

Embodiment 20. A stroke detection method operative to detect strokes suffered by mobile communication device users, the method comprising:

configuring a hardware processor, which is operative in conjunction with a mobile communication device having at least one built-in sensor, to, repeatedly and without being activated by the device's user, compare data derived from the at least one sensor to at least one baseline value for at least one indicator of user well-being, stored in memory accessible to the processor, make a stroke risk level evaluation; and perform at least one action if and only if the stroke risk level is over a threshold.

Embodiment 21. A computer program product, comprising a non-transitory tangible computer readable medium having computer readable program code embodied therein, the computer readable program code adapted to be executed to implement a method operative to detect strokes suffered by mobile communication device users, the method comprising:

configuring a hardware processor, which is operative in conjunction with a mobile communication device having at least one built-in sensor, to, repeatedly and without being activated by the device's user, compare data derived from the at least one sensor to at least one baseline value for at least one indicator of user well-being, stored in memory accessible to the processor, make a stroke risk level evaluation; and perform at least one action if and only if the stroke risk level is over a threshold.

Embodiment 22. The system of any of the preceding embodiments wherein the hardware processor comprises all or any subset of:

a passive signal component operative, typically continuously, to extract signals from at least one the built-in sensor and feed the signals into at least one other component such as the condition estimation component;

a condition estimation component which at least once estimates the user's condition, an action component which takes action depending on a current state of the user condition estimation component; and a validation component, triggered by the action component and configured to generate active signals which in turn feed into the condition estimation component.

Embodiment 23. The system of any of the preceding embodiments wherein at least one of the components comprises logic configuring a hardware processor such as the phone's own processor.

The system also includes the following embodiments;

Embodiment 101. A continuously active system (or method or computer program product) for detecting a risky medical condition of a user based on outputs generated by sensors within a device (say: smartphone) held by the user.

Embodiment 102. A system (or method or computer program product) according to any embodiment described herein wherein analysis performed by the system includes all or any subset of: motion analysis, visual analysis, audio/speech analysis e.g. detecting slurred speech by computational analysis of recorded speech using the device, user interface interaction analysis e.g. detecting systematic neglect of user interface elements appearing on the right or on the left).

Embodiment 103. A system (or method or computer program product) according to any embodiment described herein wherein at least one sensor within the smartphone captures at least one signal used for the system's analysis, only when the sensor is triggered.

Embodiment 104. A system (or method or computer program product) according to any embodiment described herein wherein a "screen on" event triggers the camera.

Embodiment 105. A system (or method or computer program product) according to any embodiment described herein wherein the medical condition comprises a stroke.

Embodiment 106. A system (or method or computer program product) according to any embodiment described herein wherein the system contacts at least one remote entity, if the risky medical condition is detected.

Embodiment 107. A system (or method or computer program product) according to any embodiment described herein wherein the system includes a processing unit configured for: identifying the user's activity and/or his interaction with the device and signal extraction from the available sensors' data.

Embodiment 108. A system (or method or computer program product) according to any embodiment described herein wherein the system comprises a cellapp downloaded onto the device by a user thereof.

Embodiment 109. A system method or computer program product) according to any embodiment described herein wherein, if the system assesses moderate risk prior to a period of end-user inactivity predicted to be long, a trigger rate of sensors is increased, whereas if the risk level is low and the user activity level is predicted to be high, the trigger rate is decreased, or configured to be lower.

Embodiment 1010. A system (or method or computer program product) according to any embodiment described herein wherein different signals are extracted depending at least in part on activities and/or interactions identified by the processing unit.

Embodiment 1011. A system (or method or computer program product) according to any embodiment described herein wherein availability of signals is determined by the processing unit at least partly as a function of the device's position.

Embodiment 1012. Processing circuitry comprising at least one processor and at least one memory and configured to perform at least one of or any combination of the described operations or to execute any combination of the described modules.

Embodiment 1013. Apparatus or methods or computer program products substantially as shown and described herein or substantially as illustrated in any of the drawings.

Embodiment 1014. Apparatus or methods or computer program products substantially as shown and described herein with realtime monitor and/or alerts.

Embodiment 1015. Apparatus or methods or computer program products substantially as shown and described herein wherein at least some computations are effected locally.

Embodiment 1017. Apparatus or methods or computer program products substantially as shown and described herein wherein a validation stage is provided for risk verification.

Also provided, excluding signals, is a computer program comprising computer program code means for performing any of the methods shown and described herein when the program is run on at least one computer; and a computer program product, comprising a typically non-transitory computer-usable or -readable medium e.g. non-transitory computer-usable or -readable storage medium, typically tangible, having a computer readable program code embodied therein, said computer readable program code adapted to be executed to implement any or all of the methods shown and described herein. The operations in accordance with the teachings herein may be performed by at least one computer specially constructed for the desired purposes, or a general purpose computer specially configured for the desired purpose by at least one computer program stored in a typically non-transitory computer readable storage medium. The term "non-transitory" is used herein to exclude transitory, propagating signals or waves, but to otherwise include any volatile or non-volatile computer memory technology suitable to the application.

Any suitable processor/s, display and input means may be used to process, display e.g. on a computer screen or other computer output device, store, and accept information such as information used by or generated by any of the methods and apparatus shown and described herein; the above processor/s, display and input means including computer programs, in accordance with all or any subset of the embodiments of the present invention. Any or all functionalities of the invention shown and described herein, such as but not limited to operations within flowcharts, may be performed by any one or more of: at least one conventional personal computer processor, workstation or other programmable device or computer or electronic computing device or processor, either general-purpose or specifically constructed, used for processing; a computer display screen and/or printer and/or speaker for displaying; machine-readable memory such as flash drives, optical disks, CDROMs, DVDs, BluRays, magnetic-optical discs or other discs; RAM s, ROMs, EPROMs, EEPROMs, magnetic or optical or other cards, for storing, and keyboard or mouse for accepting. Modules illustrated and described herein may include any one or combination or plurality of a server, a data processor, a memory/computer storage, a communication interface (wireless (e.g. BLE) or wired (e.g. USB)), a computer program stored in memoir/computer storage.

The term "process" as used above is intended to include any type of computation or manipulation or transformation of data represented as physical, e.g. electronic, phenomena which may occur or reside e.g. within registers and/or memories of at least one computer or processor. Use of nouns in singular form is not intended to be limiting; thus the teen processor is intended to include a plurality of processing units which may be distributed or remote, the term server is intended to include plural typically interconnected modules running on plural respective servers, and so forth.

The above devices may communicate via any conventional wired or wireless digital communication means, e.g. via a wired or cellular telephone network or a computer network such as the Internet.

The apparatus of the present invention may include, according to certain embodiments of the invention, machine readable memory containing or otherwise storing a program of instructions which, when executed by the machine, implements all or any subset of the apparatus, methods, features and functionalities of the invention shown and described herein. Alternatively or in addition, the apparatus of the present invention may include, according to certain embodiments of the invention, a program as above which may be written in any conventional programming language, and optionally a machine for executing the program such as but not limited to a general purpose computer which may optionally be configured or activated in accordance with the teachings of the present invention. Any of the teachings incorporated herein may, wherever suitable, operate on signals representative of physical objects or substances.

The embodiments referred to above, and other embodiments, are described in detail in the next section.

Any trademark occurring in the text or drawings is the property of its owner and occurs herein merely to explain or illustrate one example of how an embodiment of the invention may be implemented.

Unless stated otherwise, terms such as, "processing", "computing", "estimating", "selecting", "ranking", "grading", "calculating", "determining", "generating", "reassessing", "classifying", "generating", "producing", "stereo-matching", "registering", "detecting", "associating", "superimposing", "obtaining", "providing", "accessing", "setting" or the like, refer to the action and/or processes of at least one computer/s or computing system/s, or processor/s or similar electronic computing device/s or circuitry, that manipulate and/or transform data which may be represented as physical, such as electronic, quantities e.g. within the computing system's registers and/or memories, and/or may be provided on-the-fly, into other data which may be similarly represented as physical quantities within the computing system's memories, registers or other such information storage, transmission or display devices or may be provided to external factors e.g. via a suitable data network. The term "computer" should be broadly construed to cover any kind of electronic device with data processing capabilities, including, by way of non-limiting example, personal computers, servers, embedded cores, computing system, communication devices, processors (e.g. digital signal processor (DSP), microcontrollers, field programmable gate array (FPGA), application specific integrated circuit (ASIC), etc.) and other electronic computing devices. Any reference to a computer, controller or processor is intended to include one or more hardware devices e.g. chips, which may be co-located or remote from one another. Any controller or processor may for example comprise at least one CPU, DSP, FPGA or ASIC, suitably configured in accordance with the logic and functionalities described herein.

Any feature or logic or functionality described herein may be implemented by processor/s or controller/s configured as per the described feature or logic or functionality, even if the processor/s or controller/s are not specifically illustrated for simplicity. The controller or processor may be implemented in hardware, e.g., using one or more Application-Specific Integrated Circuits (ASICs) or Field-Programmable Gate Arrays (FPGAs) or may comprise a microprocessor that runs suitable software, or a combination of hardware and software elements.

The present invention may be described, merely for clarity, in terms of terminology specific to, or references to, particular programming languages, operating systems, browsers, system versions, individual products, protocols and the like. It will be appreciated that this terminology or such reference/s is intended to convey general principles of operation clearly and briefly, by way of example, and is not intended to limit the scope of the invention solely to a particular programming language, operating system, browser, system version, or individual product or protocol. Nonetheless, the disclosure of the standard or other professional literature defining the programming language, operating system, browser, system version, or individual product or protocol in question, is incorporated by reference herein in its entirety.

Elements separately listed herein need not be distinct components and alternatively may be the same structure. A statement that an element or feature may exist is intended to include (a) embodiments in which the element or feature exists; (b) embodiments in which the element or feature does not exist; and (c) embodiments in which the element or feature exist selectably e.g. a user may configure or select whether the element or feature does or does not exist.

Any suitable input device, such as but not limited to a sensor, may be used to generate or otherwise provide information received by the apparatus and methods shown and described herein. Any suitable output device or display may be used to display or output information generated by the apparatus and methods shown and described herein. Any suitable processor/s may be employed to compute or generate information as described herein and/or to perform functionalities described herein and/or to implement any engine, interface or other system illustrated or described herein. Any suitable computerized data storage e.g. computer memory may be used to store information received by or generated by the systems shown and described herein. Functionalities shown and described herein may be divided between a server computer and a plurality of client computers. These or any other computerized components shown and described herein may communicate between themselves via a suitable computer network.

The system shown and described herein may include user interface/s e.g. as described herein which may for example include all or any subset of: an interactive voice response interface, automated response tool, speech-to-text transcription system, automated digital or electronic interface having interactive visual components, web portal, visual interface loaded as web pages or screen/s from server/s via communication network/s to a web browser or other application downloaded onto a user's device, automated speech-to-text conversion tool, including a front-end interface portion thereof and back-end logic interacting therewith. Thus the term user interface or "UI" as used herein includes also the underlying logic which controls the data presented to the user e.g. by the system display and receives and processes and/or provides to other modules herein, data entered by a user e.g. using her or his workstation/device.

BRIEF DESCRIPTION OF THE DRAWINGS

Example embodiments are illustrated in the various drawings. Specifically.

An example main flow of the system herein is shown in FIG. 2, according to an embodiment. All or any subset of the illustrated operations may be provided, suitably ordered e.g. as shown, optionally in combination with all or any subset of the operations illustrated in FIG. 9 and/or in combination with all or any subset of the operations illustrated in FIG. 10.

Figure 1:
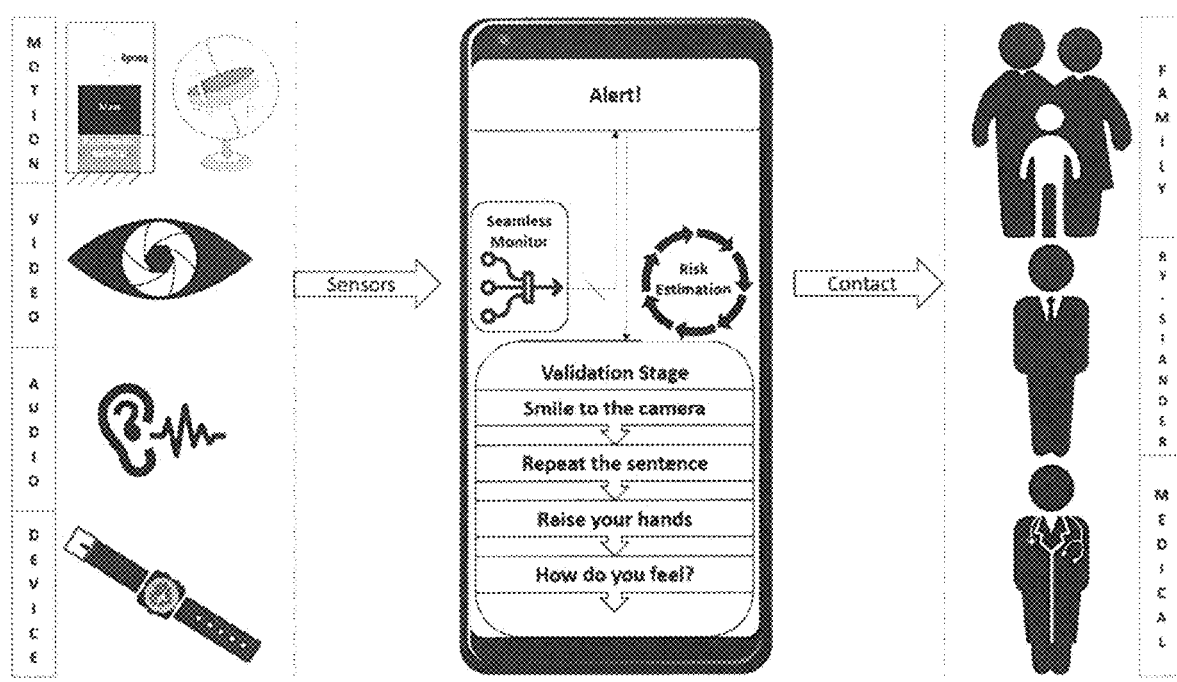
FIG. 1 is a simplified semi-block diagram semi-pictorial illustration of a system constructed and operative in accordance with an embodiment of the invention.

Another example main flow of the system herein is shown in FIG. 9, according to an embodiment.

Another example main flow of the system herein is shown in FIG. 10, according to an embodiment.

FIG. 11 describes a method for generating or developing or configuring components, all or any subset of which may be provided (e.g. may be implemented in software and may be downloaded onto an end-user's cellphone) in accordance with certain embodiments e.g. as described herein.

Certain embodiments of the present invention are illustrated in the following drawings; in the block diagrams, arrows between modules may be implemented as APIs and any suitable technology may be used for interconnecting functional components or modules illustrated herein in a suitable sequence or order e.g. via a suitable API/Interface. For example, state of the art tools may be employed, such as but not limited to Apache Thrift and Avro which provide remote call support. Or, a standard communication protocol may be employed, such as but not limited to HTTP or MQTT, and may be combined with a standard data format, such as but not limited to JSON or XML.

Methods and systems included in the scope of the present invention may include any subset or all of the functional blocks shown in the specifically illustrated implementations by way of example, in any suitable order e.g. as shown. Flows may include all or any subset of the illustrated operations, suitably ordered e.g. as shown. Tables herein may include all or any subset of the fields and/or records and/or cells and/or rows and/or columns described.

In the swim-lane diagrams, it is appreciated that any order of the operations shown may be employed rather than the order shown, however preferably, the order is such as to allow utilization of results of certain operations by other operations by performing the former before the latter, as shown in the diagram.

Computational, functional or logical components described and illustrated herein can be implemented in various forms, for example, as hardware circuits such as but not limited to custom VLSI circuits or gate arrays or programmable hardware devices such as but not limited to FPGAs, or as software program code stored on at least one tangible or intangible computer readable medium and executable by at least one processor, or any suitable combination thereof. A specific functional component maybe formed by one particular sequence of software code, or by a plurality of such, which collectively act or behave or act as described herein with reference to the functional component in question. For example, the component may be distributed over several code sequences such as but not limited to objects, procedures, functions, routines and programs and may originate from several computer files which typically operate synergistically.

Each functionality or method herein may be implemented in software (e.g. for execution on suitable processing hardware such as a microprocessor or digital signal processor), firmware, hardware (using any conventional hardware technology such as Integrated Circuit technology) or any combination thereof.

Functionality or operations stipulated as being software-implemented may alternatively be wholly or fully implemented by an equivalent hardware or firmware module and vice-versa. Firmware implementing functionality described herein, if provided, may be held in any suitable memory device and a suitable processing unit (aka processor) may be configured for executing firmware code. Alternatively, certain embodiments described herein may be implemented partly or exclusively in hardware in which case all or any subset of the variables, parameters, and computations described herein may be in hardware.

Any module or functionality described herein may comprise a suitably configured hardware component or circuitry. Alternatively or in addition, modules or functionality described herein may be performed by a general purpose computer, or, more generally, by a suitable microprocessor, configured in accordance with: methods shown and described herein, or any suitable subset, in any suitable order, of the operations included in such methods, or in accordance with methods known in the art.

Any logical functionality described herein may be implemented as a real time application, if, and as appropriate, and which may employ any suitable architectural option, such as but not limited to FPGA, ASIC or DSP or any suitable combination thereof.

Any hardware component mentioned herein may in fact include either one or more hardware devices e.g. chips, which may be co-located or remote from one another.

Any method described herein is intended to include within the scope of the embodiments of the present invention, also any software or computer program performing all or any subset of the method's operations, including a mobile application, platform or operating system e.g. as stored in a medium, as well as combining the computer program with a hardware device to perform all or any subset of the operations of the method.

Data can be stored on one or more tangible or intangible computer readable media stored at one or more different locations, different network nodes, or different storage devices at a single node or location.

It is appreciated that any computer data storage technology, including any type of storage or memory and any type of computer components and recording media that retain digital data used for computing for an interval of time, and any type of information retention technology, may be used to store the various data provided and employed herein. Suitable computer data storage or information retention apparatus may include apparatus which is primary, secondary, tertiary or off-line; which is of any type or level or amount or category of volatility, differentiation, mutability, accessibility, addressability, capacity, performance and energy use; and which is based on any suitable technologies such as semiconductor, magnetic, optical, paper and others.

DETAILED DESCRIPTION OF CERTAIN EMBODIMENTS

Smart devices such as smartphones, laptops, tablets and wearables contain a rich collection of sensors, such as cameras, audio recorders, gyroscopes, accelerometers and other optical sensors. Such sensors can be used to provide high-quality signals that are strongly related to the medical conditions of a user. In recent years, these sensors have become more accurate and common, and this trend is expected to accelerate with new sensors such as thermometers being integrated within various smart devices. Software may use such sensors for remote monitoring of patients and detection of range of medical conditions, including less urgent conditions (such as minor injury) and acute emergencies as well (such as a stroke).

FIG. 1 is a simplified semi-block diagram semi-pictorial illustration of a system constructed and operative in accordance with an embodiment of the invention. The system may rely entirely on mobile phone hardware, hence may include only software (other than an optional remote central processor e.g. for storing population-level data and providing population-level updates).

The system may seamlessly monitor the user (e.g. the system collects data, without requiring the user being aware of it). The software may e.g. in background interaction with the device, and/or perform activities in conjunction with the device, and may assess the risk of medical emergencies by analyzing valuable signals e.g. by comparing just-sensed results to references available to the software e.g. to the user's baseline results or even to population norms, and compute a risk level accordingly. According to the risk level, the system typically takes action, e.g. notifies and alerts the user if the risk is low or can be handled by him, or contacts remote entities predefined by the user, such as family members, caregivers or the emergency services if the risk is high and cannot be handled by the user. As an example, a system is described that assesses the risk of stroke using smartphones. However, the same system can be used for detecting other medical conditions including but not limited to emergencies, by using smart devices.

It is appreciated that stroke detection for example, is naively considered a solved problem, because "it is easy" (sic) to detect stroke due to the well-known B.E. F.A.S.T (Balance, Eyes, Face, Arm and Speech Test) methodology which is designed for laymen. The problem is that it is not known how to ensure that laymen will actually step up to implement this methodology, despite efforts in public education. Thus, strokes still constitute the third leading cause of death in the United States, causing over 140,000 deaths annually, and worse, are the top cause of serious, long-term disability in the United States since almost 800 thousand persons have strokes each year of which about 600,000 are first attacks and only 185,000 are recurrent. Strokes are not merely an elderly problem, since almost a quarter of strokes affect persons under age 65.

Thus a particular advantage of certain embodiments herein is to rely on technology, namely a very prevalent and ubiquitous mobile sensing/alerting/processing technology, rather than relying on (or as augmenting factor i.e. in addition to relying on) human physical presence, presence of mind, and awareness, any of which may be sadly lacking, to detect this crippling and debilitating affliction. For example, a. stroke victim's smart device can alert her or him or his surroundings, e.g. via a particularly loud or unpleasant sound emitted by the victim's device or his designated family members' devices, and/or an emergency validation call to the victim from a center (to which the victim may have subscribed), can alert the victim and or his vicinity to attend to the victim, especially if public education is used to teach the public to associate the selected sound with a stroke alert. Persons other than the victim can administer the B.E. F.A.S.T test (which can be presented to them on their devices and/or on the victim's device) and/or the device can prompt the victim to provide B.E. F.A.S.T data to suitable sensors on the device itself.

it is appreciated that certain embodiments herein face a challenge of avoiding a false alarm rate which would render use of the system intolerable in some sense. However, it is also appreciated that this challenge is surmountable e.g. by working backward: determining an acceptable false alarm rate for all stakeholders (e.g. how many non-strokes per day can arrive at an emergency room without overloading the system; and/or how many alerts from subscriber devices can reach a subscription service call center daily (assuming each such alert necessitates an immediate attempt on the part of the call center to telephone the subscriber), and/or how many loud alerts which are false alarms will subscribers and/or their family members tolerate per year without discontinuing their subscriptions, and/or etc.) and then (e.g. by linear programming) design (a cocktail e.g. linear or other combination of) stroke risk detection tests and thresholds thereof and action/s taken as a function of above-threshold events, to maximize the percentage of strokes detected, given the false alarm constraints.

As shown in FIG. 1, data from various sensors, such as cameras, microphones, gyroscopes, accelerometers, wearable sensors, and user-interaction such as typing, all may serve as input for the system, which extracts significant medical signals therefrom. The signals are then used to estimate the risk of an emergency. In the case of an emergency or a high suspicion of one, the system contacts a family member, a caregiver, or the medical services. The monitoring process is typically continuous or periodic, and occurs seamlessly during interaction or activity involving the smart device and/or involving user cooperation e.g. for validation.

Figure 2:
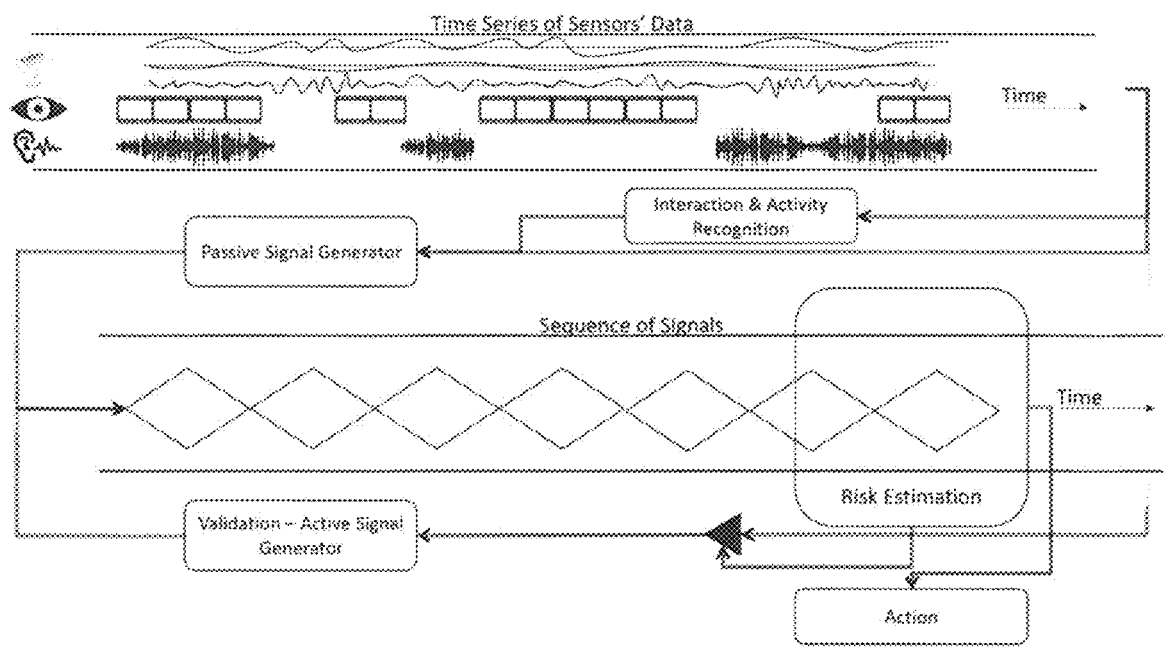

FIG. 2 shows an example monitoring process. The process may begin with the sensors' raw data recording stage, and may proceed to the activity recognition stage which may be followed by a signal generation stage that generates a sequence of signals. The system typically estimates the risk level over the signals, and may initiate an interaction with the user to enrich the signals and/or validate the risk. The risk level may then be used to determine the action to be taken e.g. alerting the user, next of kin, or emergency services, e.g. in case of a serious medical issue.

Each sensor yields unique data. Analysis of this data yields various signals that are medically significant. Examples for such signals are vital signs (e.g. all or any subset of blood pressure, heart rate, respiratory rate (or pulse), and temperature), that are extracted from wearable sensors' data, blinking rate, that is extracted from a smartphone's front camera, or a weakness in a specific part of the body, that is extracted from the motion sensors, e.g. as described below or herein. Gait analysis may include any motion signals that describe the way a user walks (e.g. all or any subset of stance duration, step rate, flexion range, etc.); alternatively, or in addition, the system may extract different signals such as hand movement range that does not describe a specific activity like walking. Thus motion sensor/s may supply gait analysis data and/or data other than gait analysis data.

Typically, signal availability depends on the user's activity and his interaction with the device. For example, typically the blinking rate can only be extracted when the user's face is in front of the front camera. Therefore, the first step in the detection process is identifying the user's activity and his interaction with the device, using the recorded data. The second step is signal extraction from the available sensors' data. The system consequently collects data from the sensors very frequently, and continuously generates a sequence of signals.

Typically, the system analyses the sequence and assesses the medical risk of stroke. In addition, the system may, at least once, e.g. depending on internal logic of the system's action component, initiate an interaction with the user, in order to collect additional data that is not available via the seamless collection process.

An example main flow of the system herein is shown in FIG. 10; another embodiment is shown in FIG. 9. Generally, it is appreciated that the system may include interacting components or functionalities, which may or may not operate in accordance with the flows of FIGS. 8 and 9; indeed all or any subset of the components may operate continuously and/or simultaneously. The components may include a passive signal component and/or a condition estimation (aka "monitoring") component which (typically continuously) estimates the user's condition, including the current risk of one or more disorders e.g. stroke, and/or an action component which takes action (e.g. generate alarm for user and/or his family member/s and/or for emergency services, change sensor timing, elicit user cooperation) depending on outputs generated by, or current state of, the user condition estimation component, and/or a validation (aka user cooperation) component, which may be triggered by the action component and may in turn generate active signals which in turn feed into the condition estimation component. Each component may comprise logic configuring a hardware processor such as the phone's own processor. The passive signal component may feed data into the condition estimation component, according to certain embodiments.

Any suitable techniques may be used for generating or developing or configuring components, e.g. as shown in FIG. 11 and/or as described with respect to any embodiment herein. The method of FIG. 11 typically includes all or any subset of the following operations, suitably ordered e.g. as shown:

Operation 1110: Definition of signal generation functions used to extract signals from the raw data e.g. when a signal is available; and/or training the generation of signals e.g. using a Machine learning algorithm Operation 1120: determine settings of condition estimation automat; component/functionality e.g. Definition of states and/or fitting the automat dynamics: transition between states and probability functions of signals' values typically including optimization of signal likelihood, using suitable machine learning algorithms such as a hidden Markov model or any other suitable method for parameter fitting e.g. as per any embodiment described herein.

Operation 1130: Implementation of actions e.g. define logic for all or any subset of User cooperation test, User notifications, Service to contact with, contextual information including what to collect and when, Timing mechanism of the sensors e.g. determine frequency of sensor activation for each of plural levels of risk.

Using the numbering of FIG. 10, for convenience, it is appreciated that the system's main flow may include all or any subset of the following operations, in any suitable order e.g. as shown:

a0. system collects offline information such as medical history, age, gender, etc., for example, in a UI window that opens on the first use of an app that the system is integrated within. For example, the system herein may operate in conjunction with a cell app; mobile phone users may subscribe to this app and be prompted to enter their offline information immediately thereafter, using a suitable online questionnaire.

This may occur, for example, for all end-users which have subscribed to a stroke alert service e.g. in order to obtain a reduction of their insurance policy premiums. Each end-user may also be asked to provide contact information of designated family members/next of kin.

When the system is activated for the first time, the user may be prompted to take tests which are typically the same as performed in validation operation e.

a. monitoring: Data from sensors, if active, flow into system.

b1. data from operation a is used to identify user's activity type (speaking, device interaction, and motion activities, such as: running, walking, bicycling . . . ). Multiple activities may be detected since they can occur concurrently.

b2. data from operation a compared to the activities detected in b1 is used to identify device position (static, in hand, in wearable e.g. bag, in hip pocket).

c1. Deduce (extract from tables) which signals are available (=there is data flow) given b1 and b2.

c2. extraction of signals deemed available in operation c1, from sensors' data from operation a.

d. Signals from c2 and, if available, at least one output from operation e may be used by system to repeatedly or constantly or periodically estimate risk of emergency (or conditional probability, given all information available, of any other condition) e.g. using ML (machine learning) sequence models such as hidden Markov models or DL sequence prediction (recurrent neural networks aka RNN, or long short-term memory (LSTM) in particular). Data may be collected in offline studies, e.g. of known stroke patients or other "labelled" end-users.

The system may employ machine learning for extracting signals such as loss of balance, walking with numbness, facial signals, speech signals etc.) rather than for directly detecting (say) stroke.

e. if the risk estimated in operation d triggers a threshold condition e.g. exceeds a threshold, system optionally notify the user of his condition and/or trigger a demand to user to participate in eliciting enriching information to validate risk.

System goes back to d. Typically, operations such as d, e and f are active simultaneously and interact with each other: for example, the condition estimation may get signals continuously and may activate the action component which may continuously monitor contextual information. Contextual information may include all or any subset of user's location, time of the day, day of the week (e.g. weekend vs. weekday vs. holiday), whether the user is at home or outside, driving, public transportation, cooperating with the system, or not.

f. System collects contextual info such as location, and access of medical services to the user g. If risk estimated in operation d (or e since operation e may go back to d) fulfils a threshold condition e.g. is categorized to, say, a $4^{th}$ or $5^{th}$ risk level out of say 5 levels), system contacts family member, caregiver or medical services taking into account the contextual situation collected in operation f.

h. Risk estimated in operation d or e is used by system to determine a timing mechanism or schedule by which to trigger sensor activation. Typically, high risk yields a schedule which triggers sensor activation more frequently, relative to lower risk levels which yield a schedule which triggers sensor activation less frequently.

It is appreciated that conventional mobile phones have APIs which, for each for each smartphone operating system e.g. android and IOS, allow cell apps to turn the sensors on and off or regulate their sampling frequency.

All or any subset of the above operations, or of the operations in FIGS. 2 and 9, may take place concurrently.

Examples of Implementations of the Operation Flow Described Above, Appear Below.

Embodiments described below may or may not be provided and may be combined in any suitable combination.

The component of passive signals and its flow is described, starting from listing possible sensors and data types produced thereby; all or any subset of these may be collected by the system. A process is then described of identifying the user's activity and interaction; all or any subset of the operations may be employed. It is explained how different activities and interactions may determine which signals are available, and may, therefore, be extracted. This is followed by an explanation of the framework for developing the functions that generate the signals from the sensors' raw data for the engineers who build such a system. Then, user cooperation and tests for generating active signals are described.

Third, condition estimation functionality is described, which processes the sequence of signals (passive and active). It is described how this functionality may update the user's baseline values (his norms), and may estimate his condition e.g. continuously. Then the action component is described, e.g. how this functionality may take contextual information into account and/or may activate the user cooperation component and/or may change sensors' triggering, and/or may alarm the user and his surroundings. Contextual information may include all or any subset of user's location, time of the day, day of the week (e.g. weekend vs. weekday vs. holiday), whether the user is at home or outside, driving, public transportation, cooperating with the system or not.

Typically, each signal has its own baseline. For example, the flexion range (while walking) signal's baseline may comprise a suitable (e.g. naïve) estimation of the flexion range values of the user when he walks. This estimation may be stored as parameters. For example, if the estimation may be assumed to have a normal distribution, the estimation can be described by (hence the baseline may include) the average flexion range and the flexion range's standard deviation.

An example Passive Signals' Flow is now described in detail.

Example sensors and data types they produce (e.g. for allowing data to flow into system in monitoring operation a in FIG. 10) are described herein. Five example sensors' data types are described, all or any subset of which may be used, including motion data e.g. from IMU, visual data from camera, audio data recorded by phone microphone, user-device interaction logs, and dedicated sensors for health monitoring (i.e. vital signs). However, the system is not limited to these listed sensors, therefore more data types generating new kinds of measurements may be included. It is appreciated that an inertial measurement unit (IMU) is intended to include any electronic device that derives and reports force and/or angular rate and/or orientation, based on sensed data collected by one or more accelerometers and/or gyroscopes, and/or magnetometers.

Figure 3:
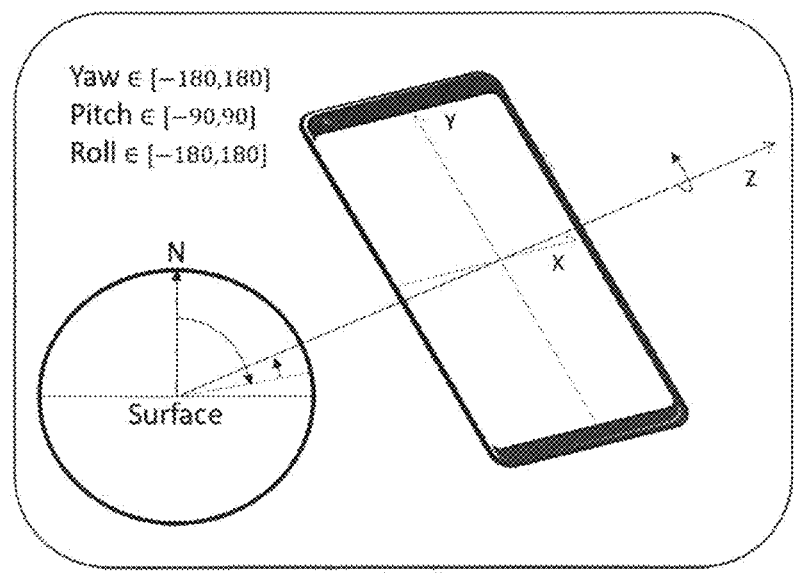
FIG. 3 is a diagram useful in understanding certain embodiments.

In FIG. 3, the device's motion is typically comprised of (all or any subset of) six different measures—three accelerations, e.g. measured relative to the device's frame of reference, and three angles that can be inferred from the device's frame of reference's orientation relative to the Earth's frame of reference (even if the north estimation is inaccurate or unknown).

Figure 4A:
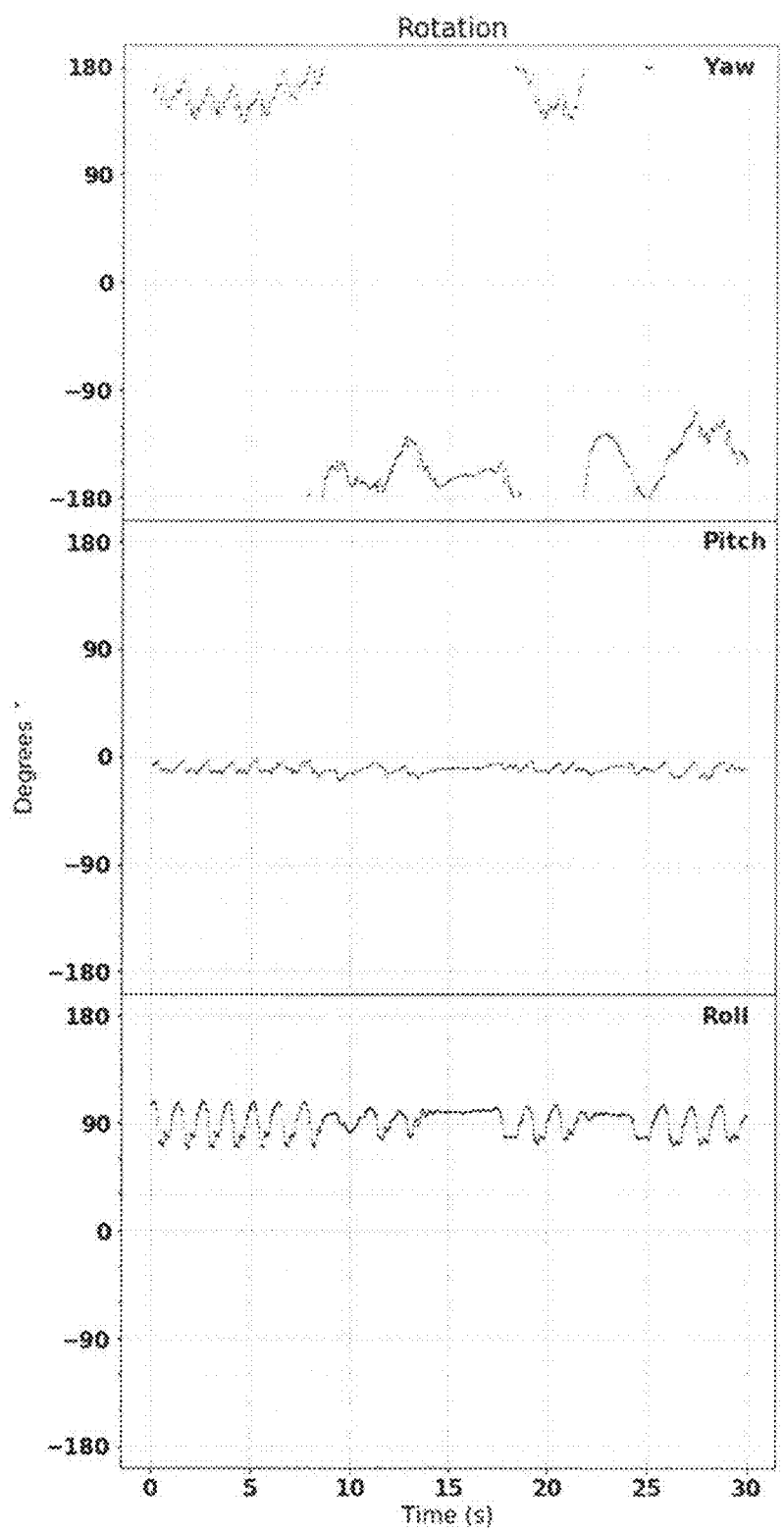
FIG. 4a illustrates rotation graphs, for the x, y and z components respectively of the mobile device's motion.
Figure 4B:
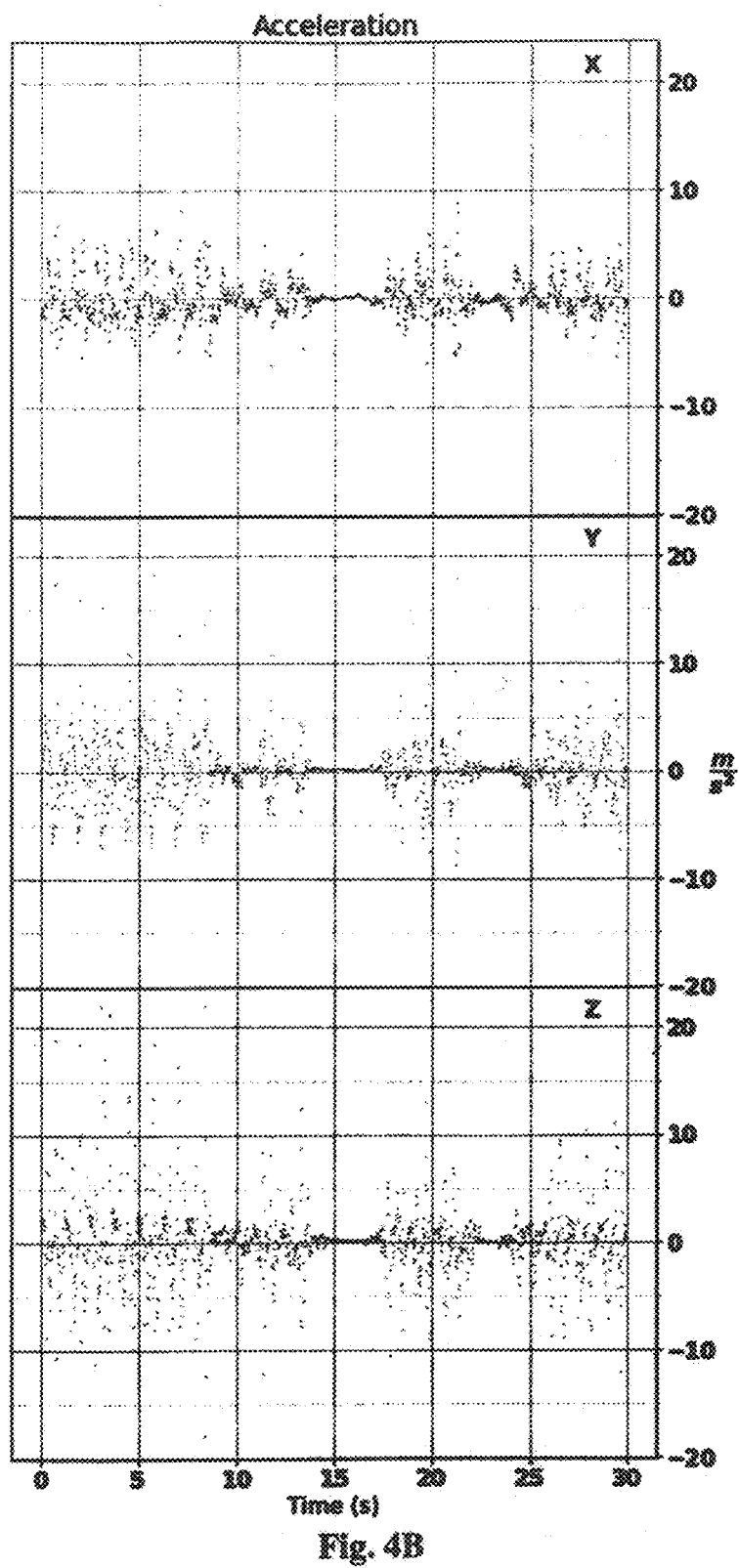
FIG. 4b illustrates acceleration graphs, for the x, y and z components respectively of the mobile device's motion.

FIGS. 4a-4b illustrate an example result of the six different measures e.g. rotation and acceleration in each of axes x, y and z (see FIG. 3) that characterize a device's motion. These measurements were taken when the mobile device was located in a pocket of a walking person.

Typically, the motion raw data is provided by the device's motion sensors such as accelerometers, gyroscopes, gravity sensors, and rotational vector sensors. Most smartphones from a variety of manufacturers have those kinds of sensors. FIGS. 4a-4b illustrate visualization of the motion raw data (acclerometers+gyro).

Typically, the visual data is a series of standard media files recorded by the camera. It can be captured in different resolution, frequency, and formats. It may inter alia be triggered when the user uses the device e.g. when the user turns on the device's screen, because it generates visual measurements of the face.

Typically, the audio data is a series of standard audio files recorded by the microphone. It can be captured in different frequency and formats as well. It is usually triggered when the user is asked to provide an audio sample in a user interactive interface (for example, during validation)

Typically, user interaction logs describe the user's action when he interacts within a user interactive interface. In this scope, the validation stage is referred to as a user interactive interface.

An integrated monitoring device is, typically, a wearable device, and its signals vary in type and sample rate. For example, a heat beat rate signal can be generated constantly by a wellness watch device such as, say, "Lintelek Fitness Tracker, Heart Rate Monitor Activity Tracker with Connected GPS Tracker, Step Counter, Sleep Monitor, IP67 Waterproof Pedometer for Android and iOS Smartphone", available from Amazon.com.

User Activity Recognition (e.g. for operation b in the main flow of FIG. 10) is now described in detail, according to certain embodiments. User activities may be divided into motion activities, speaking, and device interaction. Device interaction is typically based on the activation of the device's screen and user interaction records. Speaking detection includes the task of voice activity detection (VAD) and speaker recognition; both have several COTS solutions such as KALDI—a toolkit for speech recognition written in C++, or TarsosDSP—a library for audio processing implemented in Java.

Motion activity classification has no complete or adequate COTS solution. Motion activity classification typically includes identification of the device position (whether it is in a pocket or held) and a variety of unique motion activities. For example, it is possible to distinguish between various possible motion activities, and various possible positions of the device. Possible activities may include all or any subset of: walking, climbing up/down stairs, running, sitting down, lying down, standing up, biking, whether by bicycle or motorcycle, driving, talking on the phone, interacting with the phone. The possible positions may include all or any subset of: the static position, for example, in which the device is on the table, the hip pocket position in which the device is within the user's hip pocket, the holding position in which the device is held in the user's hand, the bag (aka "within carryable") position in which the device is in the user's bag, on the floor of the car, on the seat of the train, the shirt or the jacket pocket, strapped to the arm, and other possibilities.

Typically, when the device is static, this does not reveal anything about the user's activity, so this position does not provide any measurement (but it is easier to detect, e.g. in FIGS. 3, 4a-4b, when the device is static, all six measurements are constant, and the acceleration is zero). There are many different motion activities, each one of them having its own characteristics and thus its signals. For example, walking is characterized by the length of steps of both legs, the speed of significant junction movements such as hip, knee, and foot, and more. These quantities are signals which can be compared to their baseline values. Most of these activities have characteristics of the motion of the "full body" (or the mass center), and characteristics of the leg and the arm characteristics separately. When the device is in a pocket e.g. hip pocket, it is possible to determine both full body measurements and leg measurements. When the device is held, it is possible to determine both full body measurements and arm measurements. However, when the device is in the user's bag, only full body measurements are possible.

As shown in FIGS. 5a-7b, different device motion during walking, when the device is within the pocket, compared to in the user's bag and held, is noticeable. From this motion the system typically extracts the position of the smartphone, compared to the user's body and the activity type. This is done for instance, by using a recurrent neural network trained to classify all positions and activities described above.

Figure 5A:
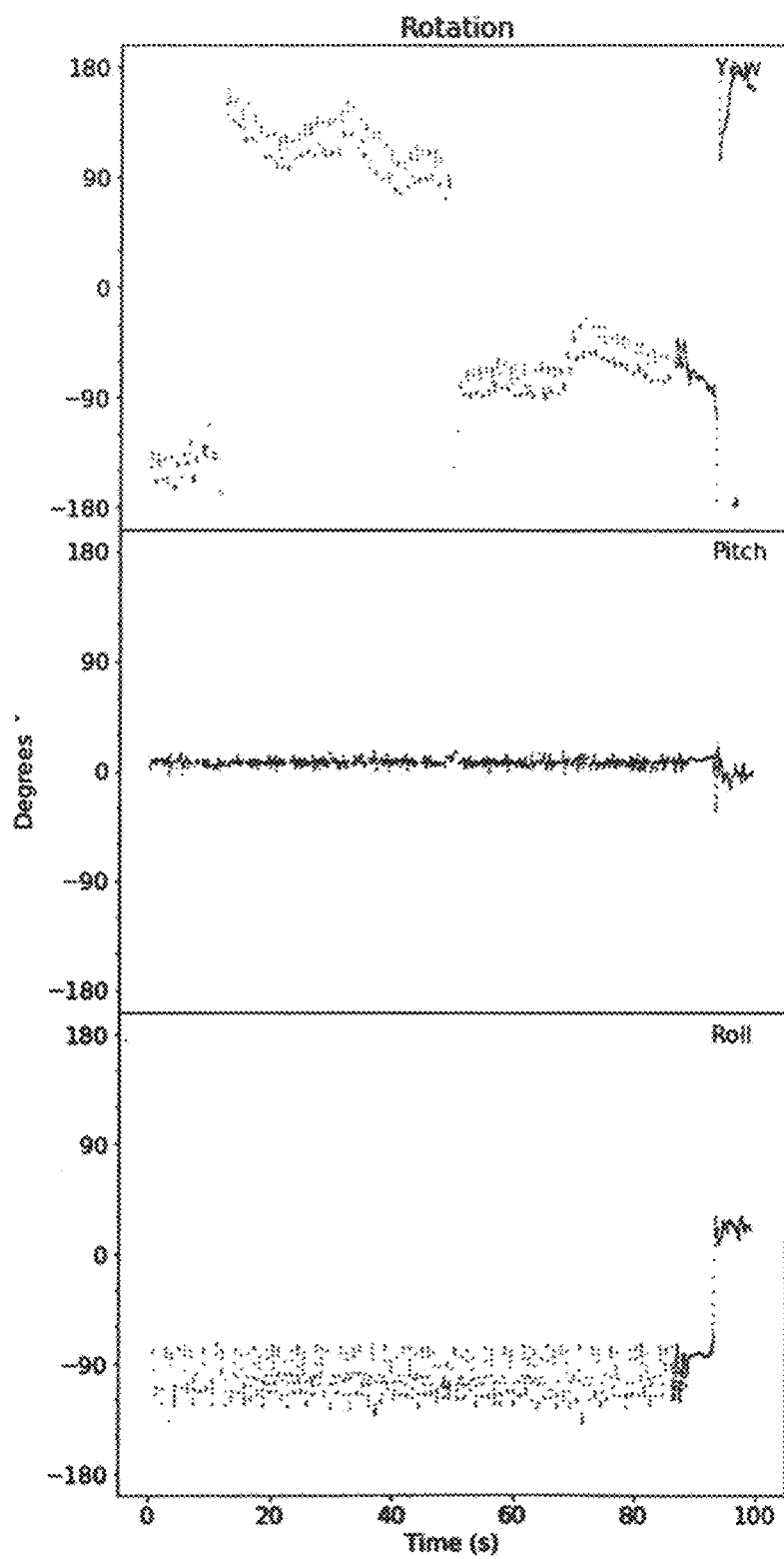
FIG. 5a illustrates rotation graphs, for the x, y and z components respectively of the mobile device's motion, where the device is in the user's pocket.
Figure 5B:
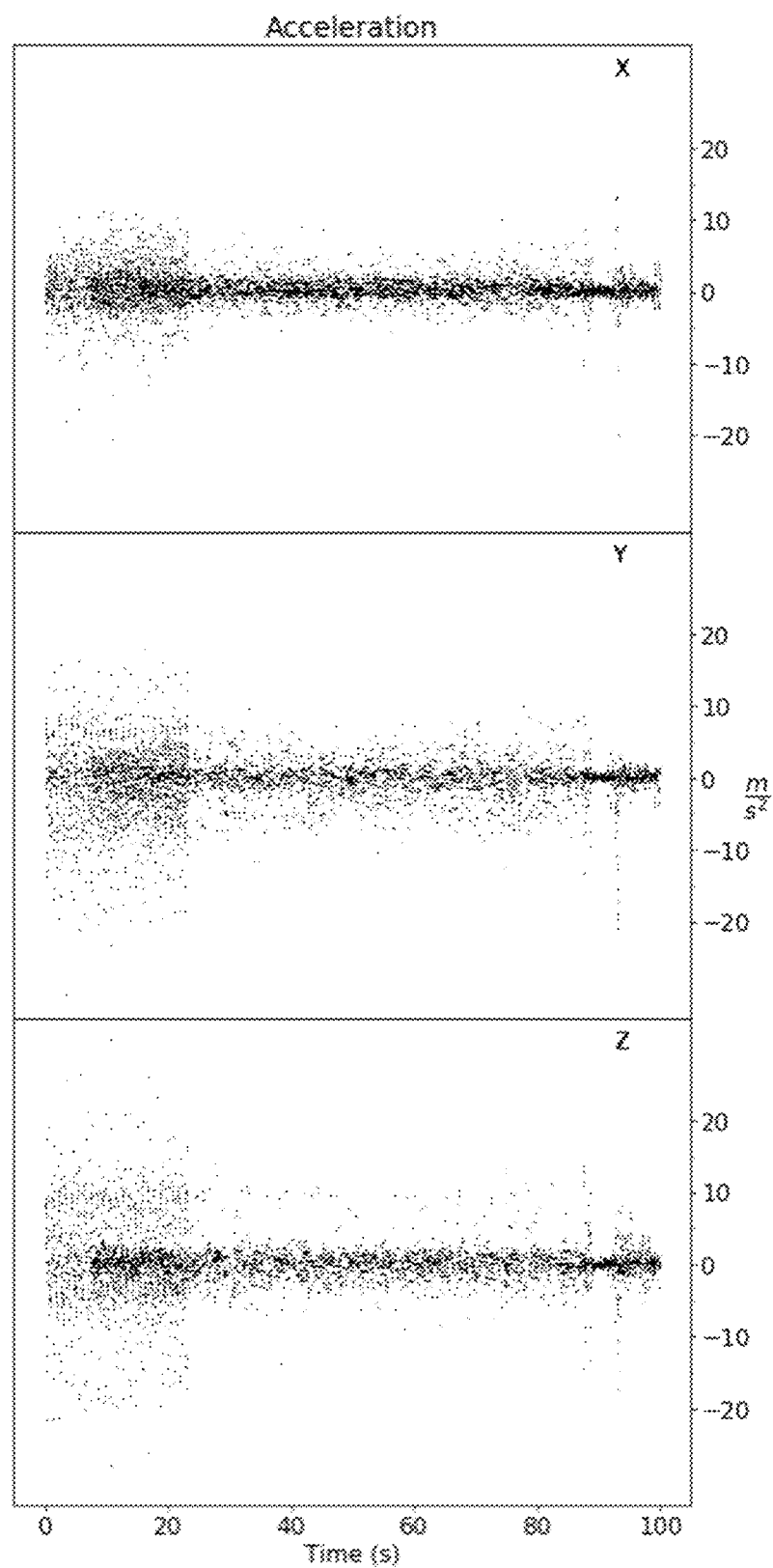
FIG. 5b illustrates acceleration graphs, for the x, y and z components respectively, of the mobile device's motion, where the device is in the user's pocket.
Figure 6A:
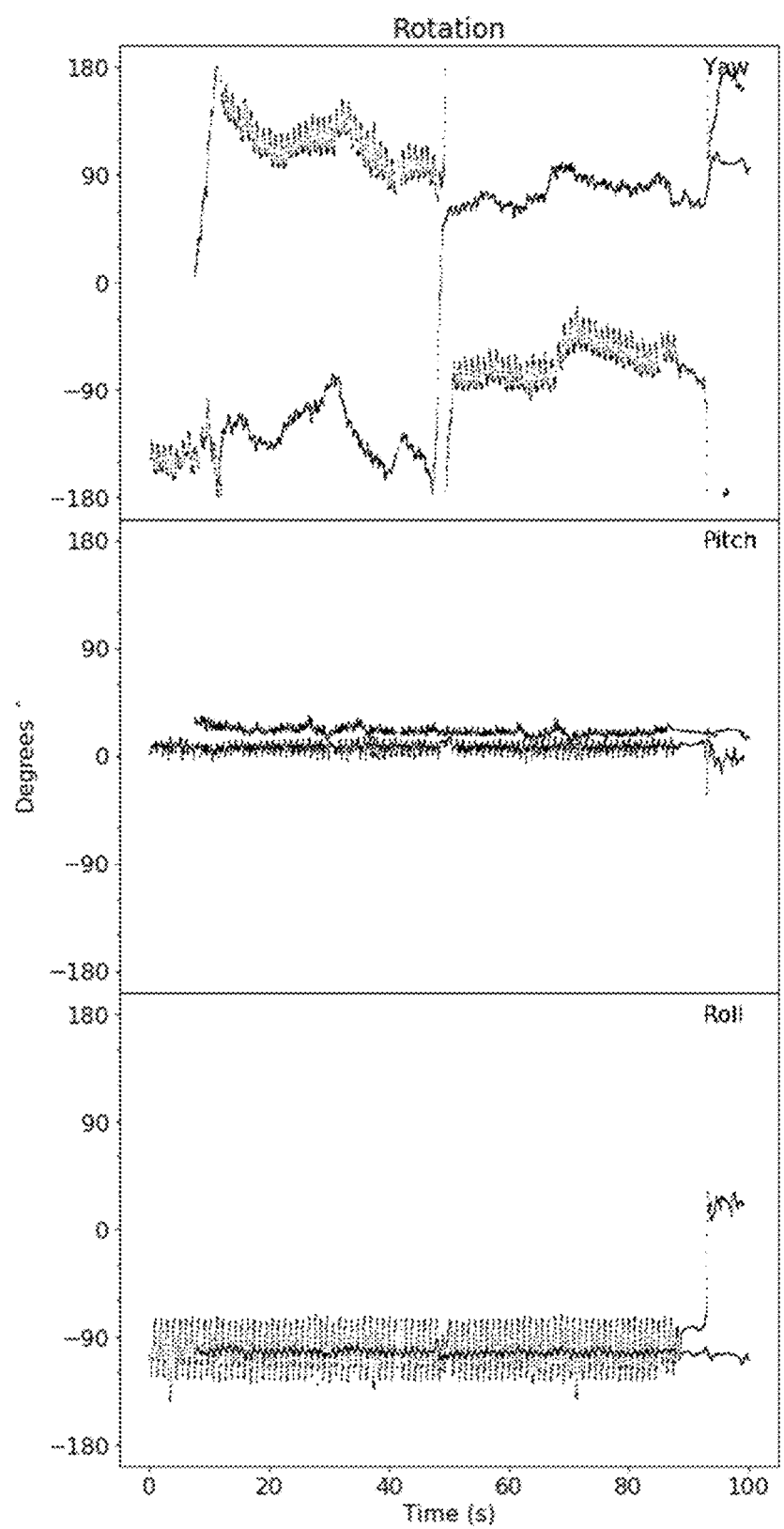
FIG. 6a illustrates rotation graphs, for the x, y and z components respectively of the mobile device's motion, where the device is in the user's backpack.
Figure 6B:
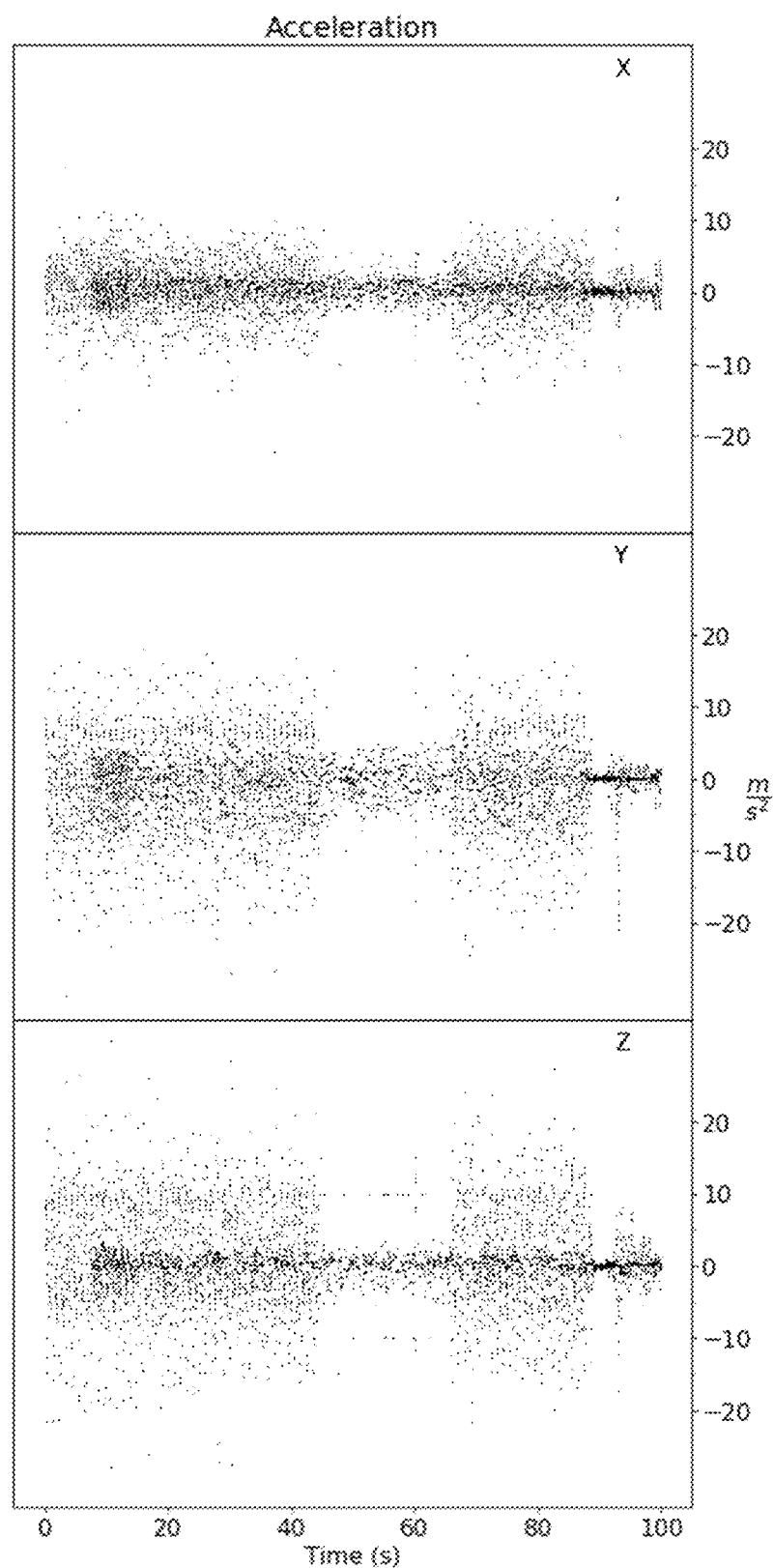
FIG. 6b illustrates acceleration graphs, for the x, y and z components respectively of the mobile device's motion, where the device is in the user's backpack.
Figure 7A:
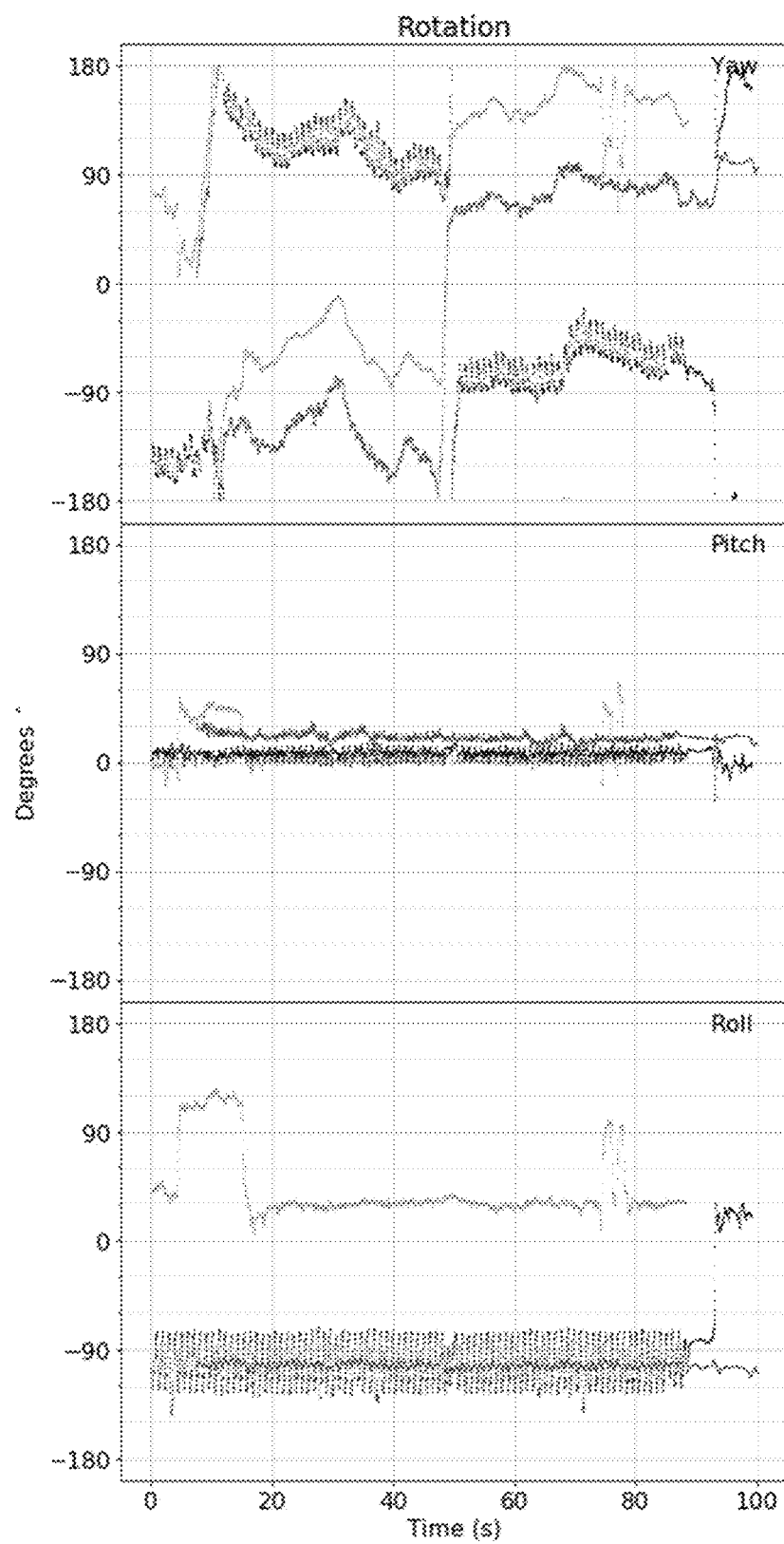
FIG. 7a illustrates rotation graphs, for the x, y and z components respectively of the mobile device's motion, where the device is in the user's hand.
Figure 7B:
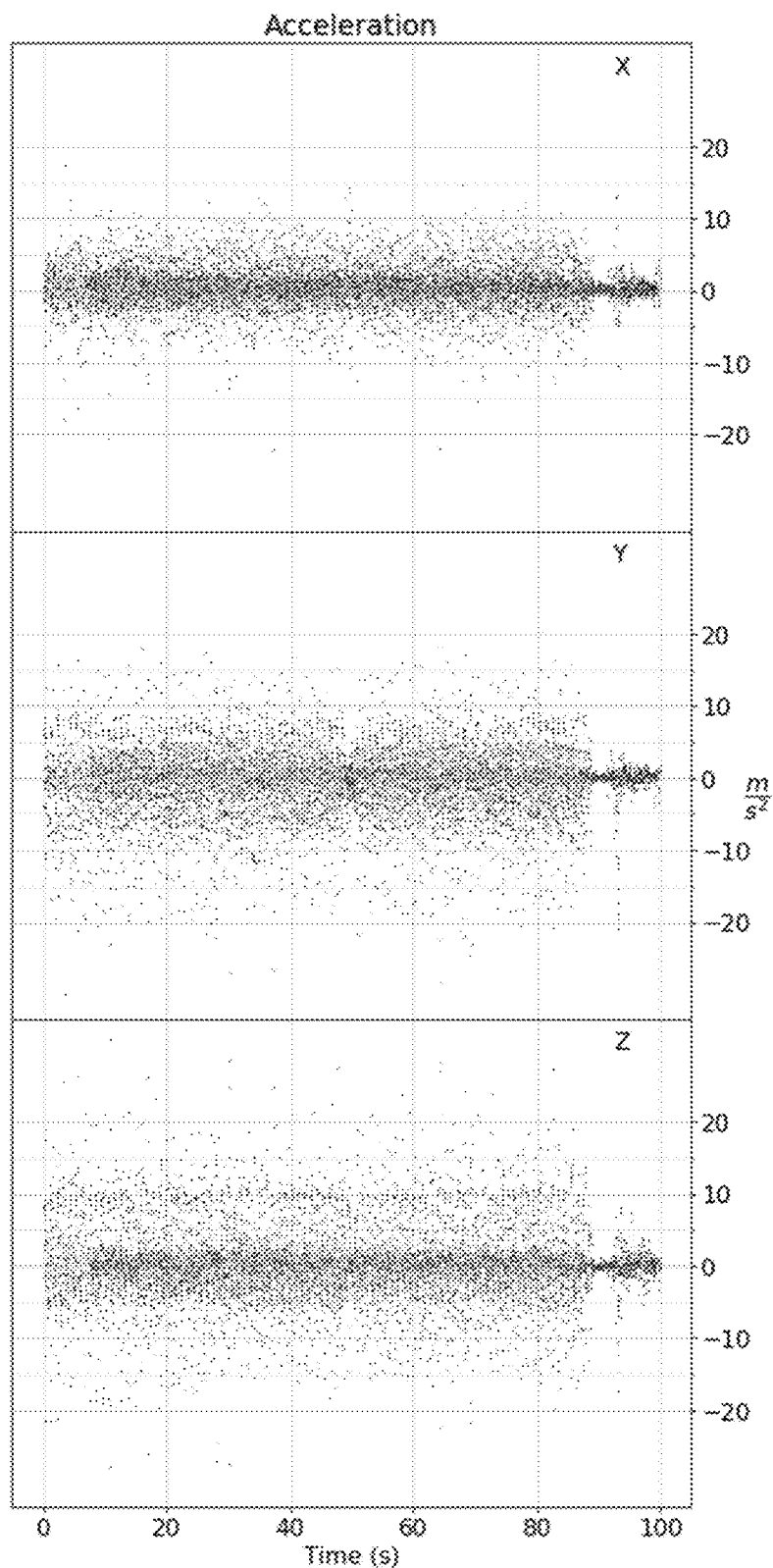
FIG. 7b illustrates acceleration graphs, for the x, y and z components respectively of the mobile device's motion, where the device is in the user's hand.

Graphs of the same measurements shown in FIGS. 4a-4b, taken from a walking person, are shown in FIGS. 5a 7b, but in these figures, the device is located inside the mobile phone user's backpack (FIGS. 6a-6b), as opposed to the device being in the phone user's pocket (FIGS. 5a-5b), as opposed to the device being in the phone user's hand (FIGS. 7a-7b). All three measurements were recorded concurrently, with similar smartphones and OS version.

Extraction of Signals (e.g. for operation c1 in the passive signals flow) is now described in detail, according to certain embodiments. In different user activities, different signals are available. Examples of signals for each activity are provided, which may be used for estimation or evaluation of a user's current medical condition or risk. An example process of extracting such signals is described further below. Values such as the mean value, standard deviation, and range of each signal, may be computed over a short period or window of time, for example 1 or a few minute/s, or a few seconds.

Figure 8A:
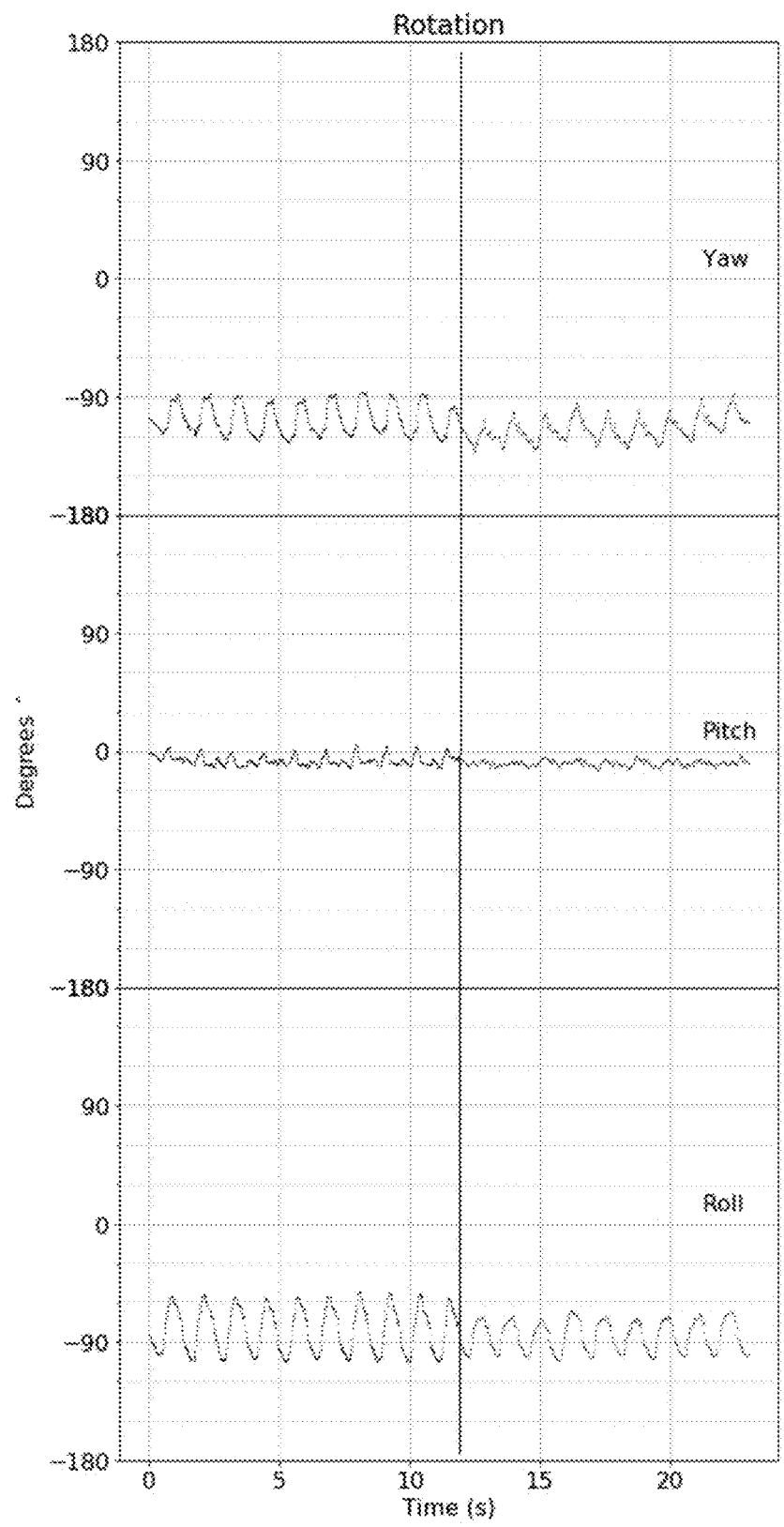
FIG. 8a illustrates rotation graphs, for the x, y and z components respectively of the mobile device's motion, when the user of the device begins to limp.
Figure 8B:
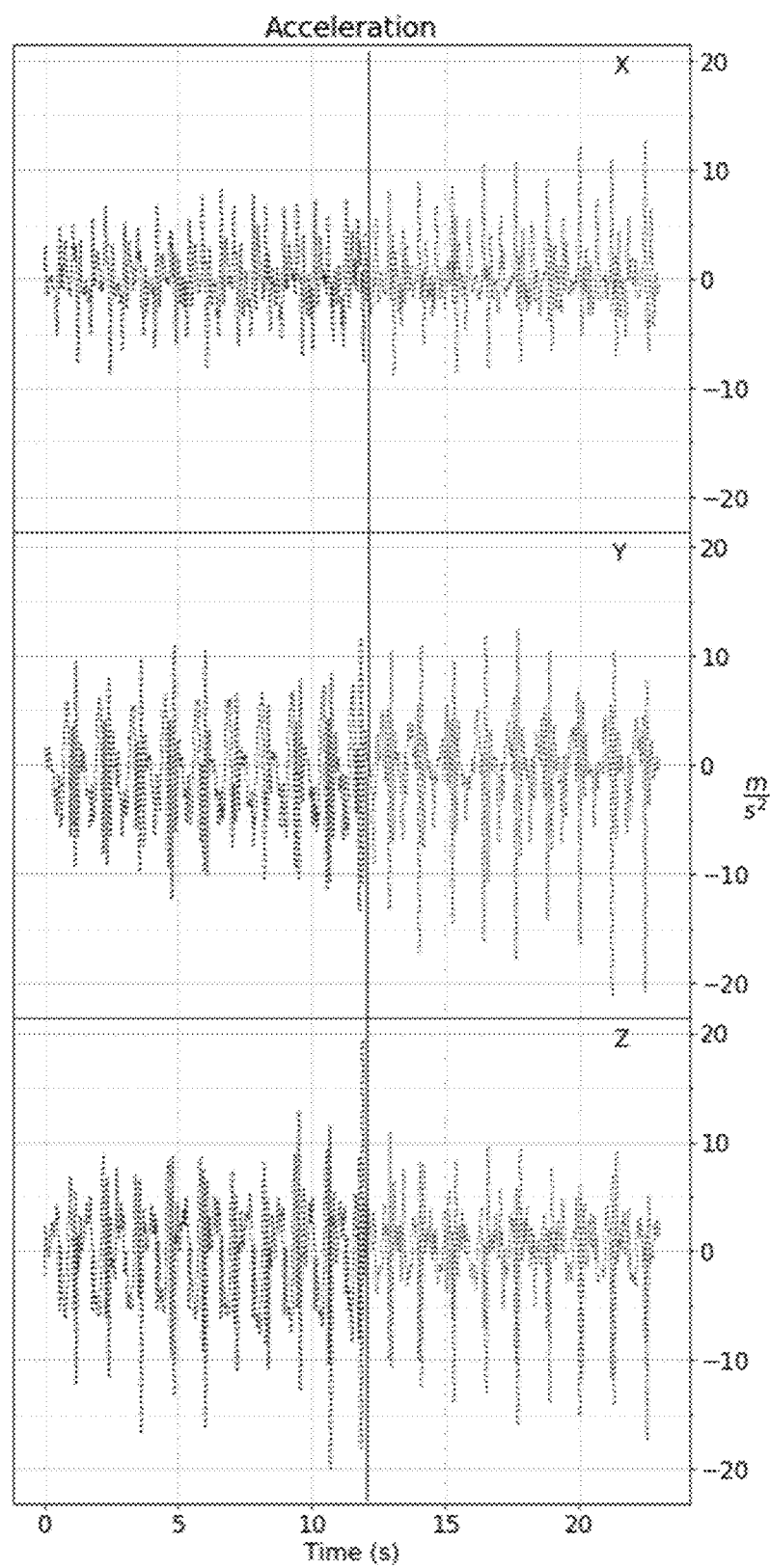
FIG. 8b illustrates acceleration graphs, for the x, y and z components respectively of the mobile device's motion, when the user of the device begins to limp.

FIGS. 8a-8b show the same measurements of FIGS. 3, 4a-4b, taken from a walking person who starts to limp after approximately 12 seconds. The change in motion at the point where the mobile phone user begins to limp, indicating in the graphs by a vertical line added to the graph, is noticeable hence can be derived e.g. numerically or computationally from accumulated motion data. This is merely an example of extracting a motion signal from a motion recording.

When a user engages in "significant" motion activities (i.e. walking, running), the device is usually inside the user's pocket, in his hands, in a hag or in the user's hand if the user is interacting with the device. Different activities may yield different signals. In addition, the device's position determines their availability. All motion signals may be extracted from the amplitude and/or shape of the device's accelerometers and/or rotation sensors. Examples of motion signals which may be used for gait analysis parameters are all or any subset of:

1. The mean and standard deviation of the step length for each leg when the subject is walking.
2. Temporal parameters (means and standard deviations) such as stance and swing duration relative to the whole stride duration, and comparison between left and right (right stance duration versus left stance duration for instance).
3. Angle ranges: flexion, extension, abduction and rotation of the thigh (means and SDs).
4. Dysfunction detection, such as hiking gait and circumduction gait.
5. The mean and standard deviation of force exerted by different leg muscles in different activities.
6. Walking/running pace range, tendency to move (e.g. a number of steps as a function of time), and other movement trends.

Any suitable method may be used to extract gait parameters E.G. stance duration, step rate, flexion range, etc. The means and the standard deviations—aka SDs—are values of the signals which may be used as input of the condition estimation component (operation d). For example, if someone begins to limp, this would indicate that his right and left stance durations' means would start to differ from each other, and the SDs would increase. The condition estimation may be configured to detect this change.

When a user engages in "gesture" motion activities (i.e. typing or holding the phone), examples of signals are:

1. Range of forces exerted on the phone; and/or
2. Range and pace of hand/arm movement.

During user interaction activities (e.g. while the user is interacting with her or his phone), the user's face can typically be recorded by the device's front camera. Examples of visual signals which may be provided by suitable image-processing of an image of the user's face include all or any subset of:

1. Facial asymmetry scores, such as sentiment analysis and muscle groups collective motion tendency, pace and range. For example, conventional sentiment analysis may be applied separately to each of the two sides of a face, and the outputs of this analysis may be compared to determine whether they are significantly different, suggesting facial asymmetry e.g. facial drop on the left but not on the right or vice versa.
2. Quantification of facial asymmetry based on 2D image/s of the face can use any suitable known technique, such as those described in
https://www.ncbi.nlm.nih.gov/pubmed/24507934
or https://www.ncbi.nlm.nih.gov/pubmed/24041610.
3. Dysphagia, or difficulty to swallow, analyzed by the swallowing rate, tendency and pattern.
4. Blinking rate of each eye.
5. Pupil size, focus, and movement.
6. Respiration rate, tendency, and range via visual indications.

For example, for stroke detection: facial drop and/or facial movement of each side of the face, or comparison of either or both, between one side of the face and the other, may be used.

Beside visual signals, interaction activities provide user interaction signals such as typing speed on the device's keyboard, and tendency to type. Moreover, the interaction activities may include some cognitive measures such as "neglect"—a phenomenon of ignoring the left or the right side of the visual field. For example, the mobile phone may be used to display to a patient aka end-user, an image which has one type of content on its right, and another on its left (e.g. an image half of which shows a night scene, say on the left, and the other half of which shows a day scene, say on the right. The system may then ask the patient if he sees day or night or "other". An end-user suffering from one-side neglect will respond that he sees a day scene, or a night scene.

For audio activities, the user speaks within the device's microphone detection range. Examples of signals include all or any subset of:

1. Base voice frequency and deviations from it.
2. Syllable sharpness analysis.
3. Speaking habits and tendency to speak.
4. Volume (range).
5. Speaking rate.

Typically, vital signs are continuously extracted from different wearables if these are available. Available wearables must be declared during the device's installation process. Examples of such include all or any subset of:

1. Heart rate range and pulse shape.
2. Oxygen saturation.
3. Blood pressure.
4. Blood sugar and alcohol levels.

In addition, phone usage metrics are typically, constantly collected. These include, for example, all or any subset of:

1. Battery usage.
2. Screen-on/screen-off/touch events time and tendency.
3. Device location.

Typically, these metrics shed light on the activity, behaviors and tendencies of the user and therefore are highly relevant for predicting future availability of signals and risk levels. For example, the distance to the nearest hospital is inferred from the location, and the active hours are inferred from the screen-on/screen-off events.

A process for learning to extract signals is now described in detail; this process may be used for example to develop the functions of operation c2 in FIG. 10. Another example for use of this process is when a user engages in "gesture" motion activities (i.e. typing or holding the phone), and it is desired to extract signals such as:

1. Range of forces exerted on the phone; and/or
2. Range and pace of hand/arm movement.

More generally, the process described below may be used to extract any signal, parameter or variable described herein, from raw data generated by phone sensors.

Typically, in order to extract signals from the raw data, the system uses special functions called "signal generation functions". These functions get, as input, the raw data and output signals. These functions include a suitably trained machine learning model. These functions may be trained using general users' data. For example, typically, producing a step length from motion measurement of a walking person requires observations of enough motion data of walking people, but does not require observations of motion data of ill people only. Signals are not pathological, but some medical cases have certain values of signals which are more likely than usual, compared to the subject's baseline values.

In order to learn such functions, typically, when designing the system herein, designers may collect some labeled data of signal values. For example, the signal function that generates a respiration rate out of audio data needs (the algorithm that fits the signal function needs this) to get pairs of audio files as a time series and a matched time series of detected respirations. These kinds of data sets may be obtained manually. e.g. when designing the system. Labelling to obtain such data sets may include asking a human to listen to many audio files of breathing people. Even a layman can detect when an inhale starts and an exhale ends—therefore, the layman can mark each breath on a timeline. These marks may be used as the labelling for breath detection and respiration rate ML algorithms. Typically, these algorithms' input includes a dataset of pairs of raw data and labels (audio files and respiration marks in time or timestamps). Typically, these algorithms' output includes a function receiving raw data and, responsively, outputting a the corresponding label (or signal value). Alternatively or in addition, the motion signals may be extracted from the amplitude and shape of the accelerometers and the rotation sensors, based on the activity type. The signal generation function is trained using series of signal values that are provided by the engineer. With the same method facial signals are extracted, using video data and standard facial landmark tracking COTS tools, such as OpenCV and DLIB.

Typically, different methods of machine learning are applied over the datasets to generate different signal functions. However, most methods are, typically, based on sequence-to-sequence prediction methods such as RNN e.g. LSTM (recurrent nets are neural networks designed to recognize patterns occurring in data sequences) from a sequence of a sensor's raw data to a sequence of labels.

An Example Active Signals' Flow is Now Described in Detail.

Validation e.g. for operation e in FIG. 10, aka user cooperation test: Validation is a type of user interaction which may be initiated by the system. Similar to the passive signals' flow, this component produces an "active" signals' flow, that feeds the user's condition monitoring aka "condition estimation" component. Typically, validation is used whenever the current evaluated risk of stroke is high or conforms to a threshold condition/criterion and is especially valuable when immediate signals are required to better assess the risk or the condition of the user. Typically, the user is notified by sound or vibration (or via integrated devices—head-speakers, smart watch and etc.) and a screen message. Repetition of the notification and alarm volume may depend on the severity of the user's condition. The alarm volume can get higher to make sure the user does not ignore it. The validation may include any suitable tests that produce various signals such as all or any subset of the following tests:
1. The user is asked to take a video of his face while smiling, which yields facial motion signals.
2. The user is asked to record audio while repeating a standard sentence, which produces speak signals.
3. The user is asked to walk with the phone in his pocket, which produces motion signals such as ruling out some medical cases, such as a limp.
4. The user is asked to hold the phone and raise the arm, for both arras, to verify that his arm motion is normal.
5. The user is asked some questions to rule out cognitive damage. For example, he is asked to describe a asymmetric photo to rule out one side "neglect".

Signals generated by the above tests may be inputs into the monitoring stage (e.g. operation a of FIG. 10).

The validation of operation e provides the system with unique, accurate and immediate data e.g. due to the high user attention. Therefore it may be used to eliminate false alarms and increase the accuracy of the system. In case the user does not respond to the validation request for more than several minutes or any other suitable time-window, the system typically treats the situation as a high risk or treats the situation as though the user had failed the validation request, with the a-priori risk evaluation determining the next action.

Each test may for example correspond to a unique UI app page, that guides the user what he is supposed to do. Alternatively, the user may be guided orally, via a suitably branching oral menu which branches depending on data collected by the system.

The Monitoring Component (aka condition estimation component) may perform monitoring and typically includes functionalities or components that, typically continuously, estimate the user's health condition, based on the available signals' values from the passive and/or active signal flow/s. Typically, monitoring is indifferent to whether the user is unaware of the system process or cooperates with the system. Firstly, how the user's condition may be estimated is described, and then how norms and/or user's baseline values may be defined and/or updated.

Risk/condition estimation (e.g. operation d in FIG. 10): the monitoring, typically, comprises a state that represents the user condition, which may include a risk, which changes across the sequence of signals; this sequence, e.g. as described above or herein, may be generated over time by any sensor available (on a mobile device). The state (e.g. risk state) determines what action to perform including contacting another person such as a family member in case of medical suspicion, or interaction with the user and/or acceleration of sensors' measurement. More frequent measurement is helpful e.g. when it is desired to track fast changes, for example, when the system detects numbness in the leg and seeks to validate that no serious limp or nerve dysfunction are starting e.g. in the event that more information of signals is needed e.g. as described below.

Typically, the risk state preserves information on the likelihood of signals' possible values, which means it determines the signals' values distribution. When the risk estimation is based on measurements of some symptoms such as limp, risk estimation typically expects to collect certain motion signals of asymmetric walking. The risk state is typically based on some symptoms or cause, and thus the risk state contains some information on the values of some signals. Hence, the state of "right leg limp" may expect to get, for the "right stance duration" signal, values that are smaller than the "left stance duration" signal's values, since when one leg is weaker than the other, people usually step less on the weaker leg.

Typically, each state (e.g. level of risk) depends on a previous state (most recent prior level of risk), on a baseline including one or more baseline values, on medical history, and on signals that have become available since the most recent prior level of risk. The risk state aka risk level evaluation typically changes to fit a level of risk (or a user's condition) which has the maximum likelihood of the current signal sequence' values. This defines the dynamics of the state transition to adapt to the optimal state continuously.

One can describe this process as a Hidden Markov Model (HMM). Typically, the risk states are hidden. Typically, their observations are the signals' values distributed by the states' definitions, and, typically, they have transition probability function from state to state. However, typically, the state set is typically not fully known e.g. including its size, the states' observation probability functions, and/or the transition probabilities from one state to another. These are parameters that typically, need to be fitted. In addition, the observations are typically, not independent given a state, rather they form a Markov chain of a bounded order.

This state automat's parameters may be initially, roughly or partially defined based on expert knowledge, and then be better fitted gradually as more data is collected. Typically, these expert-based predefined parameters are the only knowledge available to the system on the model, initially; but as data is collected by the system over time, as more and more end-users use the system, parameters, and hence estimation abilities of the system, improve in accuracy.

Learning these parameters may be performed via a suitable sequential deep learning based architecture (e.g. an LSTM for instance). Typically, the algorithm trains over the sequence of signals to predict the next signals' values. Typically, an expert-based transition function determines that at some points the state transforms to a specific state, thus, at some points, the state is known as an additional input for the training.

User's Baseline: The state's probability function of signals' values may be calibrated to the user's baseline values as different users have different values of the same signal in the same context. For example, the step length of two users during standard walking may differ. However, according to certain embodiments, the states themselves and the transition function are general over users rather than being unique per user. It may be inferred across all the users e.g. because of sample complexity (only data collected from many users for a long period of time may be enough for learning this task). Typically, it represents the general property of the dynamics.

Typically, the signal calibration process includes a representation of the user's baseline. A signal's baseline representation is a parameter (or a set of parameters) that adjusts the signal's probability function to fit the user's values in a certain state. Hence, the calibration typically takes a state, a signal and its baseline representation as arguments, and generates a probability function for the signal's values. For example, assuming that signals have normal distribution over their values, the "step length" signal's baseline typically includes the average and/or standard deviation of past step lengths, and thus implies the predicted step length distribution in the general state.

This process of calibrating the baseline may be continuous, which may mean that whenever a new signal's value gets into the monitoring component, the evaluation of the parameters is updated. Thus, for the last example of normal distributed "step length", when a new value of step length arrives the average step length and its standard deviation are updated. When the system is activated for the first time, the user may be required to take some tests for initial calibration. These tests may be the same as performed in the validation stage, described below. Calibration may occur continuously, or periodically, or from time to time.

Action Component: different actions may be taken as the state changes e.g. depending on a current state of the monitoring component. The action component of the system typically includes logic determining which action's to take: contextual information is introduced, on which at least one, or every action typically depends (e.g. while depending, in addition, also on the user's estimated condition. The action component may change sensors timing, when the component may try to initiate cooperation of the user, and the way the action component may alarm the user and his surrounding and/or may contacts others e.g. the user's family members, is also described.

According to certain embodiments, outputs of the monitoring component govern which action (e.g. change sensor timing, alarm, contact others, invite user to cooperate to validate a suspected condition) if any, is or are taken by the action component.

Actions may include all or any subset of:

a. Contextual information

Contextual information may include user's location, time of the day, day of the week, whether the user is at home or outside, driving, public transportation, cooperating with the system or not, etc. Contextual information may reflect future ability to gain new signals, and/or the way an interaction of the system may be perceived by the user and his surroundings.

Typically, the system updates contextual information periodically (e.g. continuously or every m, e.g. 5, minutes) or from time to time.

b. Sensor Timing may be changed, e.g. to optimize operation a in FIG. 10. In order to optimize battery usage, data usage, and privacy. Typically, some sensors such as camera, microphone and motion sensors, are not always on. Other sensors, say, the accelerometer sensor which is not a big battery consumer, might perhaps remain constantly on. Thus all or some sensors may, by default, be inactive, and may be triggered using a timing mechanism which depends on the current risk estimation (state), and typically, the contextual information. For example, if the system's current evaluation assesses moderate risk prior to a long-predicted time of inactivity (such as the night or other hours in which the user is frequently inactive) the system (e.g. the action component thereof) may increase the trigger rate, so the system will record the following user activity immediately. On the other hand, when the risk level is low and the user activity level is predicted to be high, the trigger rate may be configured to be lower. This may be true for a subset of the sensors and user interactions, e.g. motion and wearable sensors are always on.

c. Initiation of User's Cooperation. When the user's condition estimated in the monitoring component reflects a risk, the system optionally notify the user of his condition and/or trigger a demand to user to participate in eliciting enriching information to validate risk, which may be performed by a user cooperation component. This action may take into account contextual information, such as whether the user is active, and his location.

d. Providing Alarms and Notifications. The system can alert his surroundings and contact medical services according to the situation severity e.g. when depending on system knowledge re how risky is a given detected state or re whether or not a user is able to help himself. When the user's condition is less urgent (for example in a recovery process, system knowledge may indicate that it is sufficient for the system to provide the user with feedback about her or his activity), or the user seems to manage the situation by himself, the action component of the system may notify him of the condition e.g. by a message sound or vibration. All these actions may be determined by contextual information as well. For example, when the user is outside, he might be embarrassed to get voice feedback regarding the way he walks. Contextual information may include all or any subset of user's location, time of the day, day of the week (e.g. weekend vs. weekday vs. holiday), whether the user is at home or outside, driving, public transportation, cooperating with the system or not.

Whether or not to take certain actions and how, e.g. when to provide feedback or an alarm, e.g. to user and via which output device, may be dependent on contextual information. For example, whether or not to take certain actions, and how to do so, may depend on the user's location, e.g. not in the office, only when he is outside walking, or at home. The system may learn from user indications that he does not wish to get such feedback again in that location, and will not give him feedback when he is in that location in the future, or may give the user voice feedback with head speakers if contextual information indicates he has/is using them or through a smart-watch.

Examples of feedbacks (which may be provided in the therapist's voice) include:
  Gait recovery
    Range of motion: "nice progress! your thigh extension is better than before!", —same for flexion
    Hip balance (the effort of keeping hip horizontal).
    Circumduction gait: "Try not to take your leg from the side, and bend your knee)
  Speech
    Speech fluency—"your word tempo has increased in the last day"
    Diction—"Try to pronounce 'S' as your teeth touch each other"

Once the system is configured, and includes the integrated components of sensors, signals' generation, condition estimation, user cooperation, and various of actions depend on the condition state, the engineer typically verifies that the definition of the signal generation, the settings of the condition estimation automat, and the implementation of the actions are well defined e.g. as listed in FIG. 11 and/or as described in details in embodiments herein.

"Risk estimation" is but one use of tracking and presenting the states over time as described herein. For example, the system can be used for rehabilitation of walking abilities including alerting when the user does not strictly keep symmetric pace motions. Similarly, the system may provide any other feedback to the user, based on its tracking, to make the user has changed his behavior, e.g. to take a rest and stop walking, or to change the way he is walking, such as a suggestion or reminder to the user that s/he increase his step size or bend her/his knees more.

It is appreciated that such suggestions may, for the user, be reminders, e.g. if a therapist teaches the user to respond to these suggestions, then perhaps he/she programs the instance of the system serving that user, to provide these suggestions, perhaps responsive to certain parameters which may be extracted from the user's phone data. Some risks are significant, but temporary and infrequent for the short term. One such case is a TIA (transient ischemic attack), which is a stroke that lasts only a few minutes. TIA indicates a higher risk of having a real stroke, and thus detection of TIAs can save lives. TIAs are easy to be ignored by the subject who has them, as many stroke signals are not clear for one who is suffering from them. The system described herein, typically has the attribute for helping someone having a stroke and notifying his surrounding, and may alternatively or in addition document e.g. timestamps the incident and/or the symptoms as reflected in the described signals, and bring them to a suitable entity's attention (end user, his medical team, etc.). This documentation helps the physicians to diagnose such incidents and provide the patient with stroke prevention care.

TIA detection flow may include all or any subset of the following operations, suitably ordered e.g. as follows:
1. System detects dysfunction of walking (imbalance, stance problems, etc.), or facial drop, or problems with speech
2. System estimates a higher risk condition state
3. System notifies the user and initiates some tests ("smile to the camera", "hold the phone and raise it to the sky", "repeat the sentence")
4. If user cooperated, system updates its condition estimation, and increases its sensors' sampling
5. Otherwise the system alerts the surroundings and tries to contact family members
6. The system stores all of the signals along the incident: starting time of the walking/face/speech problem and what it was (signals and values), the results of the user tests (signals and values), and its estimation over the process. In addition, the system typically keeps (e.g. stores in memory) the raw data of the signals and tests: pictures/videos of the face, audio files of the user's speech, and his motion when he walked.
7. When the user goes back to fully functional behavior, he can watch this documentation and/or show the documentation to a specialist.

Many use cases are possible, such as but not limited to the following:
1. Stroke Detection for High-Risk Population
A high-risk population user downloads and installs a special app. He enters some relevant information when he registers, such as age and gender, and medical conditions such as dysfunction of some leg or hand as a result of previous stroke (stage 0). The app monitors his motion through the accelerometer very frequently (one minute every five minutes) or even continuously (stage a). When the app detects a repetitive pattern (stage b), it triggers the gyroscope to collect more details of the motion (stage h & stage a). Given the full motion data (accelerations and orientations from the gyro), the app recognizes the user's activity and the device's bodily position (stage b). Besides monitoring the user's motion, the app collects videos of his face each time he interacts with the app (and hence he watches the screen and the front camera supposedly— stage a & b), and moreover it listens (recording via the mic) all the time (stage a), and when it recognizes his voice (stage b) it records him to make a further analysis. According to the data, the app has collected (motion, video, voice-stage a), and the activity of the user and the bodily position of the device (stage b), it deduces which parameters are available and extracts them (stage c): If the user walks, it extracts gait parameters such as temporal parameters (such as stance duration of the two legs and their symmetry), spatial parameters (such as clearance, flexion, and extension), and others. If it has collected a video of the user's face, it extracts facial motoric parameters, such as the motion of the edges of his mouth, and, if such is collected, it extracts parameters from speech, such as speaking tempo and sharpness. The app estimates the risk of the user from those parameters' values over time (stage d). If it has recognized a limp, or dysfunction of the facial motorics, or weakness in speech, its suspicion increases. When there is a suspicion the app tries to interact with the user and asks him to take a quick test according to the data that would provide it with more certainty (stage e), such as measuring the user's walking, range of motion and force of his arms, his ability to repeat some words, or smile (every test has a clear UI window, that explains the test and activates the relevant sensor). This gives the app additional parameters' values to validate its estimation of risk (stage d). If the risk is high, the app alerts the user, and according to contextual information (stage f) such as location and whether the user interacts with it or not, the app contacts family members, bystanders, and medical services by sending messages, placing calls, and notifying the surroundings loudly via the phone. The app continues to collect data and estimate the user's condition.

For example, in this use case or any other, the system may attract the attention of a bystander near a suspected stroke victim, whose stroke risk evaluation is high, by generating an alarm which differs from the alarm which a phone would generally use to alarm the phone user himself e.g. an alarm which is louder than any alarm used to alarm the phone user himself, and/or an alarm otherwise distinguishable from conventional alarms used to alarm the phone user himself, such as perhaps an oral warning, "potential emergency, please help". Thus, even if (e.g. due to bystander privacy considerations) the system does not know who is standing near a stroke victim, there is hope that if there is such a bystander, he would hear the alarm and respond.

2. Walking Rehabilitation

A user that does a recover process, downloads and installs a special app. He enters certain relevant information when he registers, such as age and gender, and medical conditions such as dysfunction of some leg or hand as a result of a stroke or an accident (stage 0). The app monitors his motion through the accelerometer very frequently (one minute every five minutes) or even continuously (stage a). When the app detects a repetitive pattern (stage b), it triggers the gyroscope to collect more details of the motion (stage a). Given the full motion data (accelerations and orientations from the gyro), the app recognizes the user's activity and the device's bodily position (stage b). According to the activity and the bodily position, it deduces which parameters are available and extracts them (stage c): If the user walks or goes up/down the stairs, it extracts gait parameters such as temporal parameters (like stance duration of the two legs and their symmetry), spatial parameters (such as clearance, flexion, and extension) and others. The app stores the user's parameters' values in a remote database to reflect his progress and trends of each parameter for him—through a UI dashboard in the app, and for his physical therapist through a special therapist dashboard which is accessible only to him (using a password) in a web page. The app (or a connected component in a server) continuously analyzes the change in the parameters (stage d), and gives the user real-time feedback (stage e), such as to bend his knee more, or to increase his step length, or slow down. This feedback can be customized by the therapist (to fit it to feedback he uses to give in his clinic, and which the user understands). For instance, in order to define feedback, the therapist has a definition UI tool, in which he determines the valid value range for each parameter, and the feedback to give when the parameter's value exceeds the range (above and below), in text, voice, and a notification sound or vibration. Moreover, the user can be notified with the feedback in different ways according to contextual information the app constantly collects (stage t), such as private or public locations, surrounding noise and etc. In addition, the app can suggest to the user to do certain exercises (stage e) to give him more feedback and to measure his parameters when he is aware of the measurement. A notification to start an exercise is also triggered by contextual information to fit the user's convenience.

3. Speech Therapy for Children

A child with difficulties in pronouncing words and phonemes, and who wishes to improve his diction, downloads and installs a special app. He enters certain relevant information when he registers, such as age and gender, and some specific difficulties such as pronouncing (stage 0). The app continuously records audio (stage a) and tries to recognize his voice and speech (stage b). When the child's voice is detected, it deduces which parameters are available and extracts them (stage c) such as words tempo, and the quality of pronouncing spoken phonemes. The app stores the child's parameters' values in a remote database to reflect his progress and trends of each parameter for him—through a UI dashboard in the app, and for his speech therapist through a special therapist dashboard which is accessible only to him (using a password) in a web page. The app (or a connected component in a server) continuously analyzes the change in the parameters (stage d), and gives the user real-time feedback (stage e), such as to keep pronouncing 'L' the way he has just done. This feedback can be customized by the therapist (to fit it to feedback he uses to give in his clinic, and which the user understands). For instance, in order to define feedback, the therapist has a definition UT tool, in which he determines the valid value range for each parameter, and the feedback to give when the parameter's value exceeds the range (above and below. or if the parameter's value is binary, for example, pronounced good or not—just define the feedback for true and false values), in text, voice, and a notification sound or vibration. Moreover, the user can be notified with the feedback in different ways according to contextual information the app constantly collects (stage f), such as private or public locations, surrounding noise and etc. In addition, the app can suggest the user do some exercises (stage e) to give him more feedback and to measure his parameters when he is aware of the measurement. A notification to start an exercise is also triggered by contextual information to fit the user's convenience. For example, the app can open a small exercise when the user is at home (based on GPS) and he is free (just playing with the phone), and gives him a challenging sentence to repeat it.

4. Mental Supportive Tool

A user downloads and installs an app. He enters certain relevant information when he registers, such as age and gender, and medical conditions, such as depression. The app monitors his motions through the accelerometer, periodically (stage a). When the app detects a repetitive pattern (stage b), it triggers the gyroscope to collect more details of the motion (stage a). Given the full motion data (accelerations and orientations from the gyro), the app recognizes the user's activity and the device's bodily position (stage b). Besides monitoring the user's motion, the app collects videos of his face each time he interacts with the app (and hence he watches the screen and the front camera supposedly—stage a & b), and moreover it listens (recording via the mic) all the time (stage a), and when it recognizes his voice (stage b) it records him to make a further analysis. According to the data the app has collected (motion, video, voice—stage a), and the activity of the user and the bodily position of the device (stage b), it deduces which parameters are available and extracts them (stage c): If the user walks, it extracts gait parameters such as temporal parameters (such as step rate and stance duration), spatial parameters (like clearance, flexion, and extension), and others. If it has collected a video of the user's face, it extracts facial motoric parameters such as facial expressions, and if it has collected speech, it extracts parameters such as speaking tempo and sentiment. The app estimates the condition of the user from these parameters' values over time (stage d). If it has recognized a sensitivity, its concern increases. When the concern gets more significant, the app tries to interact with the user and gives him supportive words (stage e). It can also ask for nice words from friends and family set in the app settings. The app records the user's response to that interaction (response to app's notification & questions, voice, video, and motion), which gives the app additional parameters' values to validate its estimation of concern (stage d). Moreover, an interaction can be established in different ways according to contextual information the app constantly collects (stage f), such as private or public locations, surrounding noise, etc.

5. Medical Research for Evaluation of the Success of Hip Replacement Surgeries

A medical department installs the app on a group of patients' devices as a part of a study, before they have surgery. The medical coordinator enters certain relevant information when he registers the patients on a registration page in the app, such as age, gender, and medical conditions, such as pains in some relevant bodily positions (stage 0). For each user, the app monitors his motion through the accelerometer very frequently (one minute every five minutes) or even continuously (stage a). When the app detects a repetitive pattern (stage b), it triggers the gyroscope to collect more details of the motion (stage h, stage a). The app stores the user's parameters' values over time in a remote database, to be compared with values of the same parameters after the surgery.

6. Medical Research for Monitoring the Change of Behavior of People with Degenerative Diseases (such as Parkinson, Alzheimer, High Risk Population of Stroke), and Research of Understanding the Effectiveness of Relevant Medicines and Drugs.

A medical department installs the app on a group of patients' devices as a part of a study. The medical coordinator enters certain relevant information when he registers the patients on a registration page in the app, such as age, gender, and medical conditions such as that the patient suffers from Alzheimer's disease (stage 0). For each user, the app monitors his motion through the accelerometer very frequently (one minute every five minutes) or even continuously (stage a). When the app detects a repetitive pattern (stage b), it triggers the gyroscope to collect more details of the motion (stage h, stage a). Given the full motion data (accelerations and orientations from the gyro), the app recognizes the user's activity and the device's bodily position (stage b). Besides monitoring the user's motion, the app collects videos of his face each time he interacts with the app (and hence he watches the screen and the front camera supposedly—stage a & b), and moreover it listens (recording via the mic) all the time (stage a), and when it recognizes his voice (stage b) it records him to make a further analysis. According to the data, the app has collected (motion, video, voice—stage a), and the activity of the user and the bodily position of the device (stage b), it deduces which parameters are available and extracts them (stage c). According to the activity and the bodily position, it deduces which parameters are available and extracts them (stage c): If the user walks or goes up/down stairs, it extracts gait parameters such as temporal parameters (such as stance duration of the two legs and their symmetry), spatial parameters (such as clearance, flexion, and extension) and others. If it has collected a video of the user's face, it extracts facial motoric parameters such as facial expressions, and if it has collected his speech, it extracts parameters such as speaking tempo and sentiment. The app stores the user's parameters' values over time in a remote database to analyze the trends of parameters over time, and how it differs between patients that get different treatment.

7. General Health Feedback

A user downloads and installs a special app. He enters certain relevant information when he registers, such as age and gender, and medical conditions such as cardiovascular disease. The app monitors his motion through the accelerometer very frequently (one minute every five minutes) or even continuously (stage a). When the app detects a repetitive pattern (stage b), it triggers the gyroscope to collect more details of the motion (stage a). Given the full motion data (accelerations and orientations from the gyro), the app recognizes the user's activity and the device's bodily position (stage b). Besides monitoring the user's motion, the app collects data from wearables such as continuous heartbeat rate from a smartwatch, videos of his face each time he interacts with the app (and hence he watches the screen and the front camera supposedly—stage a & b), and moreover it listens (recording via the mic) all the time (stage a), and when it recognizes his voice (stage h) it records him to make a further analysis. According to the data, the app has collected (wearable data, motion, video, voice—stage a), and the activity of the user and the bodily position of the device (stage h), it deduces which parameters are available and extracts them (stage c): If the user walks, it extracts gait parameters such as temporal parameters (such as step rate and stance duration), spatial parameters (such as clearance, flexion, and extension) and others. if it has collected video of the user's face, it extracts facial motoric parameters such as facial expressions and how pale he is, and if it has collected his speech, it extracts parameters such as speaking tempo, sentiment, and hoarseness. It also collects the heartbeat rate and blood pressure from the smartwatch. The app estimates the condition of the user from those parameters' values over time (stage d). If it recognizes that the user's face is pale and his voice is hoarse, it asks him how he feels (stage e). If the user answers that he feels unwell, the app validates its concern (stage d). Then if the risk is low, it recommends the user to rest, otherwise it suggests to him to contact medical services or contacts such a service by itself according to contextual information the app constantly collects (stage f), such as private or public locations, and accessibility to a medical center.

According to certain embodiments, a single software system may provide future stroke detection, and facilitate walking and/or speech rehabilitation from a stroke already suffered; this is useful since stroke victims are prone to suffer additional strokes.

It is appreciated that terminology such as "mandatory", "required", "need" and "must" refer to implementation choices made within the context of a particular implementation or application described herewithin for clarity and are not intended to be limiting since in an alternative implementation, the same elements might be defined as not mandatory and not required or might even be eliminated altogether.

Components described herein as software may, alternatively, be implemented wholly or partly in hardware and/or firmware, if desired, using conventional techniques, and vice-versa. Each module or component or processor may be centralized in a single physical location or physical device or distributed over several physical locations or physical devices.

Included in the scope of the present disclosure, inter alia, are electromagnetic signals in accordance with the description herein. These may carry computer-readable instructions for performing any or all of the operations of any of the methods shown and described herein, in any suitable order including simultaneous performance of suitable groups of operations as appropriate.

Included in the scope of the present disclosure, inter alia, are machine-readable instructions for performing any or all of the operations of any of the methods shown and described herein, in any suitable order; program storage devices readable by machine, tangibly embodying a program of instructions executable by the machine to perform any or all of the operations of any of the methods shown and described herein, in any suitable order i.e. not necessarily as shown, including performing various operations in parallel or concurrently rather than sequentially as shown; a computer program product comprising a computer useable medium having computer readable program code, such as executable code, having embodied therein, and/or including computer readable program code for performing, any or all of the operations of any of the methods shown and described herein, in any suitable order; any technical effects brought about by any or all of the operations of any of the methods shown and described herein, when performed in any suitable order; any suitable apparatus or device or combination of such, programmed to perform, alone or in combination, any or all of the operations of any of the methods shown and described herein, in any suitable order; electronic devices each including at least one processor and/or cooperating input device and/or output device and operative to perform e.g. in software any operations shown and described herein; information storage devices or physical records, such as disks or hard drives, causing at least one computer or other device to be configured so as to carry out any or all of the operations of any of the methods shown and described herein, in any suitable order; at least one program pre-stored e.g. in memory or on an information network such as the Internet, before or after being downloaded, which embodies any or all of the operations of any of the methods shown and described herein, in any suitable order, and the method of uploading or downloading such, and a system including server/s and/or client's for using such; at least one processor configured to perform any combination of the described operations or to execute any combination of the described modules; and hardware which performs any or all of the operations of any of the methods shown and described herein, in any suitable order, either alone or in conjunction with software. Any computer-readable or machine-readable media described herein is intended to include non-transitory computer- or machine-readable media.

Any computations or other forms of analysis described herein may be performed by a suitable computerized method. Any operation or functionality described herein may be wholly or partially computer-implemented e.g. by one or more processors. The invention shown and described herein may include (a) using a computerized method to identify a solution to any of the problems or for any of the objectives described herein, the solution optionally include at least one of a decision, an action, a product, a service or any other information described herein that impacts, in a positive manner, a problem or objectives described herein; and (h) outputting the solution.

The system may if desired be implemented as a web-based system employing software, computers, routers and telecommunications equipment as appropriate.

Any suitable deployment may be employed to provide functionalities e.g. software functionalities shown and described herein. For example, a server may store certain applications, for download to clients, which are executed at the client side, the server side serving only as a storehouse. Any or all functionalities e.g. software functionalities shown and described herein may be deployed in a cloud environment. Clients e.g. mobile communication devices such as smartphones may be operatively associated with, but external to the cloud.

The scope of the present invention is not limited to structures and functions specifically described herein and is also intended to include devices which have the capacity to yield a structure, or perform a function, described herein, such that even though users of the device may not use the capacity, they are, if they so desire, able to modify the device to obtain the structure or function.

Any "if-then" logic described herein is intended to include embodiments in which a processor is programmed to repeatedly determine whether condition x, which is sometimes true and sometimes false, is currently true or false and to perform y each time x is determined to be true, thereby to yield a processor which performs y at least once, typically on an "if and only if" basis e.g. triggered only by determinations that x is true and never by determinations that x is false.

Any determination of a state or condition described herein, and/or other data generated herein, may be harnessed for any suitable technical effect. For example, the determination may be transmitted or fed to any suitable hardware, firmware or software module, which is known or which is described herein to have capabilities to perform a technical operation responsive to the state or condition. The technical operation may, for example comprise changing the state or condition, or may more generally cause any outcome which is technically advantageous given the state or condition or data, and/or may prevent at least one outcome which is disadvantageous given the state or condition or data. Alternatively or in addition, an alert may be provided to an appropriate human operator or to an appropriate external system.

Features of the present invention, including operations, which are described in the context of separate embodiments, may also be provided in combination in a single embodiment. For example, a system embodiment is intended to include a corresponding process embodiment and vice versa. Also, each system embodiment is intended to include a server-centered "view" or client centered "view", or "view" from any other node of the system, of the entire functionality of the system, computer-readable medium, apparatus, including only those functionalities performed at that server or client or node. Features may also be combined with features known in the art and particularly although not limited to those described in the Background section or in publications mentioned therein.

Conversely, features of the invention, including operations, which are described for brevity in the context of a single embodiment, or in a certain order, may be provided separately or in any suitable subcombination, including with features known in the art (particularly although not limited to those described in the Background section or in publications mentioned therein) or in a different order. "e.g." is used herein in the sense of a specific example which is not intended to be limiting. Each method may comprise all or any subset of the operations illustrated or described, suitably ordered e.g. as illustrated or described herein.

Devices, apparatus or systems shown coupled in any of the drawings may in fact be integrated into a single platform in certain embodiments or may be coupled via any appropriate wired or wireless coupling such as but not limited to optical fiber, Ethernet, Wireless LAN, HomePNA, power line communication, cell phone, Smart Phone (e.g. iPhone), Tablet, Laptop, PDA, Blackberry GPRS, Satellite including GPS, or other mobile delivery. It is appreciated that in the description and drawings shown and described herein, functionalities described or illustrated as systems and sub-units thereof can also be provided as methods and operations therewithin, and functionalities described or illustrated as methods and operations therewithin can also be provided as systems and sub-units thereof. The scale used to illustrate various elements in the drawings is merely exemplary and/or appropriate for clarity of presentation and is not intended to be limiting.

Any suitable communication may be employed between separate units herein e.g. wired data communication and/or in short-range radio communication with sensors such as cameras e.g. via WiFi, Bluetooth or Zigbee.

It is appreciated that implementation via a cellular app as described herein is but an example, and, instead, embodiments of the present invention may be implemented, say, as a smartphone SDK; as a hardware component; as an STK application, or as suitable combinations of any of the above.

Any processing functionality illustrated (or described herein) may be executed by any device having a processor, such as but not limited to a mobile telephone, set-top-box, TV, remote desktop computer, game console, tablet, mobile e.g. laptop or other computer terminal, embedded remote unit, which may either be networked itself (may itself be a node in a conventional communication network e.g.), or may be conventionally tethered to a networked device (to a device which is a node in a conventional communication network or is tethered directly or indirectly/ultimately to such a node).

Any operation or characteristic described herein may be performed by another actor outside the scope of the patent application and the description is intended to include apparatus whether hardware, firmware or software which is configured to perform, enable or facilitate that operation or to enable, facilitate or provide that characteristic.

The terms processor or controller or module or logic as used herein are intended to include hardware such as computer microprocessors or hardware processors, which typically have digital memory and processing capacity, such as those available from, say Intel and Advanced Micro Devices (AMD). any operation or functionality or computation or logic described herein may be implemented entirely or in any part on any suitable circuitry including any such computer microprocessor/s as well as in firmware or in hardware or any combination thereof.

It is appreciated that elements illustrated in more than one drawings, and/or elements in the written description may still be combined into a single embodiment, except if otherwise specifically clarified herewithin. any of the systems shown and described herein may be used to implement or may be combined with, any of the operations or methods shown and described herein.

It is appreciated that any features, properties, logic, modules, blocks, operations or functionalities described herein which are, for clarity, described in the context of separate embodiments, may also be provided in combination in a single embodiment, except where the specification or general knowledge specifically indicates that certain teachings are mutually contradictory and cannot be combined. any of the systems shown and described herein may be used to implement or may be combined with, any of the operations or methods shown and described herein.

Conversely, any modules, blocks, operations or functionalities described herein, which are, for brevity, described in the context of a single embodiment, may also be provided separately or in any suitable sub-combination, including with features known in the art. Each element e.g. operation described herein may have all characteristics and attributes described or illustrated herein or according to other embodiments, may have any subset of the characteristics or attributes described herein.

It is appreciated that apps referred to herein may include a cell app, mobile app, computer app or any other application software. Any application may be bundled with a computer and its system software or published separately. The term "phone" and similar used herein is not intended to be limiting and may be replaced or augmented by any device having a processor, such as but not limited to a mobile telephone, or also set-top-box, TV, remote desktop computer, game console, tablet, mobile e.g. laptop or other computer terminal, embedded remote unit, which may either be networked itself (may itself be a node in a conventional communication network e.g.) or may be conventionally tethered to a networked device (to a device which is a node in a conventional communication network or is tethered directly or indirectly/ultimately to such a node). Thus the computing device may even be disconnected from e.g., Wifi, Bluetooth etc. but may be tethered directly or ultimately to a networked device.

The invention claimed is:

1. A risky condition detection system operative to detect risky conditions suffered by mobile communication device users, the system comprising:
a hardware processor operative in conjunction with a mobile communication device having at least one built-in sensor; the hardware processor being configured to, repeatedly and without being activated by the device's user,
compare data derived from said at least one sensor to at least one baseline value for at least one indicator of user well-being, stored in memory accessible to the processor,
make a risk level evaluation evaluating level of risk that the user is suffering from a risky condition; and
perform at least one action if and only if the risk condition level is over a threshold,
wherein the system is configured to, at least once, activate an inactive sensor in a user's mobile phone, responsive to a current estimation of a user's condition derived from data provided by sensors other than said inactive sensor in the user's mobile phone, and to validate or modify the current estimation of a user's condition, according to outputs of the inactive sensor.

2. The system of claim 1 wherein the system initiates user cooperation to validate said evaluation and changes said evaluation for at least one user, responsive to that user's cooperation.

3. The system of claim 1 wherein the system connects to at least one additional wearable to validate said evaluation, and changes said evaluation for at least one user, responsive to data provided by said at least one additional wearable.

4. The system of claim 3 wherein said wearable comprises a smartwatch, pedometer, or heartbeat monitor.

5. The system of claim 1 wherein said at least one sensor comprises plural sensors.

6. The system of claim 5 wherein said plural sensors include at least one of the following: IMU, camera, microphone.

7. The system of claim 5 wherein said plural sensors include at least two of the following: IMU, camera, microphone.

8. The system of claim 1 wherein the system is configured to document at least one temporary infrequent symptom such as TIA.

9. The system of claim 1 wherein said sensor comprises a motion sensor.

10. The system of claim 9 wherein said motion sensor comprises at least one of: gyroscope, accelerometer.

11. The system of claim 1 wherein said sensor comprises at least one of: camera, microphone, or keypad of said communication device.

12. The system of claim 1 wherein said stroke risk level evaluation includes detection of facial asymmetry which differs from said indicator.

13. The system of claim 1 wherein said stroke risk level evaluation relies only on said at least one built-in sensor, thereby to obviate any need for any sensor not already deployed in mobile phones.

14. The system of claim 1 wherein said action comprises prompting the user to cooperate in a validation process.

15. The system of claim 1 wherein an auxiliary software platform enables recruitment of mobile phone users to subscribe to said system, thereby to allow an organization affiliated with a multiplicity of mobile phone users, to require or incentivize mobile phone users affiliated therewith to subscribe to said system.

16. The system of claim 1 wherein said data comprises gait analysis data.

17. The system of claim 16 wherein said stroke risk level evaluation includes processing said gait analysis data including detection of gait asymmetry which differs from said indicator.

18. The system of claim 1 wherein said hardware processor comprises the mobile communication device's processor, onto which cell app software has been downloaded, wherein said software is configured to:
compare data derived from said at least one sensor to at least one baseline value for at least one indicator of user well-being, stored in memory accessible to the processor,
make a stroke risk level evaluation; and
perform at least one action if and only if the stroke risk level is over a threshold.

19. The system of claim 1 wherein the hardware processor comprises all or any subset of:
a passive signal component operative, typically continuously, to extract signals from at least one said built-in sensor and feed said signals into at least one other component such as said condition estimation component;
a condition estimation component which at least once estimates the user's condition,
an action component which takes action depending on a current state of the user condition estimation component; and
a validation component, triggered by the action component and configured to generate active signals which in turn feed into the condition estimation component.

20. The system of claim 19 wherein at least one of said components comprises logic configuring a hardware processor such as the phone's own processor.

21. The system of claim 1 wherein said action performed if and only if the risk level is over the threshold comprises triggering activation of at least one sensor more frequently, relative to frequency of activation of said at least one sensor at lower risk levels.

22. The system of claim 1 wherein said risky condition comprises a stroke and wherein said risk level evaluation evaluates a level of risk that the user is suffering from a stroke.

23. A risky condition detection method operative to detect risky conditions suffered by mobile communication device users, the method comprising:
configuring a hardware processor, which is operative in conjunction with a mobile communication device having at least one built-in sensor, to, repeatedly and without being activated by the device's user,
compare data derived from said at least one sensor to at least one baseline value for at least one indicator of user well-being, stored in memory accessible to the processor,
make a risk level evaluation evaluating level of risk that the user is suffering from a risky condition thereby to provide condition estimation functionality; and
perform at least one action if and only if the risky condition level is over a threshold
wherein the condition estimation functionality takes contextual information into account and, at least one, changes sensors' triggering.

24. The method of claim 23 wherein said contextual information includes an indication of whether the user is at home.

25. The method of claim 23 wherein said contextual information is repeatedly periodically updated.

26. A computer program product, comprising a non-transitory tangible computer readable medium having computer readable program code embodied therein, said computer readable program code adapted to be executed to implement a method operative to detect risky conditions suffered by mobile communication device users, the method comprising:
configuring a hardware processor, which is operative in conjunction with a mobile communication device having at least one built-in sensor, to, repeatedly and without being activated by the device's user,
compare data derived from said at least one sensor to at least one baseline value for at least one indicator of user well-being, stored in memory accessible to the processor,
make a risk level evaluation evaluating level of risk that the user is suffering from a risky condition thereby to provide condition estimation functionality; and
perform at least one action if and only if the risky condition level is over a threshold,
wherein the condition estimation functionality takes contextual information into account and, at least one, changes sensors' triggering.

* * * * *